US005597923A

United States Patent [19]

Nagano et al.

[11] Patent Number: 5,597,923

[45] Date of Patent: Jan. 28, 1997

[54] QUINOLONE CARBOXYLIC ACID DERIVATIVES IN CRYSTALLINE HYDRATE FORM

[75] Inventors: Hiroyuki Nagano, Shizuoka; Nobuyuki Suzuki, Tokyo, both of Japan

[73] Assignee: Chugai Seiyaku Kabushiki Kaisha, Tokyo, Japan

[21] Appl. No.: 256,726

[22] PCT Filed: Jan. 31, 1993

[86] PCT No.: PCT/JP93/00109

§ 371 Date: Jul. 21, 1994

§ 102(e) Date: Jul. 21, 1994

[87] PCT Pub. No.: WO93/15070

PCT Pub. Date: Aug. 5, 1993

[30] Foreign Application Priority Data

Jan. 31, 1992 [JP] Japan .................................... 4-016545

[51] Int. Cl.$^{6}$ ...................... A61K 31/47; C07D 215/233; C07D 215/38

[52] U.S. Cl. ............................................................ 546/156

[58] Field of Search ............................. 546/156; 514/312

[56] References Cited

U.S. PATENT DOCUMENTS 5,051,509 9/1991 Nagano .................................. 546/156

FOREIGN PATENT DOCUMENTS

| | | |
|---|---|---|
| 342675 | 11/1989 | European Pat. Off. . |
| 62-252772 | 11/1987 | Japan . |
| 63-104974 | 3/1988 | Japan . |
| 63-198664 | 8/1988 | Japan . |
| 64-090184 | 4/1989 | Japan . |
| 1-090184 | 4/1989 | Japan . |
| 3-95177 | 4/1991 | Japan . |

OTHER PUBLICATIONS

Borka; *"Review on Crystal Polymorphism of Substances in the European Pharmacopoeia"* Pharm. Acta Helv.; vol. 66; No. 1; pp. 16–21; 1991.

Anwar et al; *Polymorphism of Sulfathiazole;* Journal of Pharmaceutical Sciences; vol. 78; No. 4; pp. 337–342; 1989.

Kaneniwa et al; *"Hygroscopicity of Carbamazepine Crystalline Powders"*; Yakugaku Zassi; vol. 104 (2); pp. 184–190; 1984.

Saito et al; *"Studies on the Relationship between Physico–chemical Properties and Crystalline Forms of Tulobuterol Hydrochloride. III. Hygroscopic Properties of Polymorphus of Tulobuterol Hydrochloride"*; Yakugaku Zassi; vol. 103 (3): pp. 336–341; 1983.

Yuasa et al; *"Pharmaceutical Studies on Hydrates of AM–715 Physical Characteristics and Intestinal Absorption"*; Yakugaku Zassi; vol. 102 (5); pp. 469–476; 1982.

*Primary Examiner*—C. Warren Ivy
*Assistant Examiner*—D. Margaret M. Mach
*Attorney, Agent, or Firm*—Browdy and Neimark

[57] ABSTRACT

1-Cyclopropyl-6-fluoro-1,4-dihydro-8-methoxy-7- (3-methylaminopiperidin-1-yl)-4-oxoquinoline-3-carboxylic acid dihydrate having the following formula:

F, O, COOH, N, N, $OCH_3$, $NHCH_3$, $.2H_2O$

The crystal of this dihydrate exhibits excellent stability over the other crystal forms under various pharmaceutical formulation conditions such as moisture absorption and blending in solvents and, hence, it is a most advantageous crystal form in the manufacture of pharmaceuticals.

3 Claims, 38 Drawing Sheets

TEMPERATURE CURVE
TG CURVE
808.6ug
817.6ug
8.0%
8.1%
TG ug
100.0
-150.0
-400.0
-650.0
-900.0
DTA uV
5.500
3.000
0.500
-2.000
-4.500
TEMP C
85.00
70.00
55.00
40.00
25.00
TIME min
0.0
75.0
150.0
225.0
300.0

TG ug
100.0
-150.0
-400.0
-650.0
-900.0
7.9%
825.6ug
834.6ug
8.0%
TIME min
0
350
700
1050
1400
DTA uV
5.500
3.000
0.500
-2.000
-4.500
TEMP C
85.00
70.00
55.00
40.00
25.00

TG ug
100.0
-150.0
-400.0
-650.0
-900.0
8.0%
808.5ug
5.500
3.000
0.500
-2.000
-4.500
DTA uV
85.00
70.00
55.00
40.00
25.00
TEMP C
1000
1038
1075
1113
1150
TIME min TG ug
100.0
-150.0
-400.0
-650.0
-900.0
151.6 C
51.31min
2.27uV
128.7C
43.68min
-0.27uV
90.9C
31.01min
-5.65uV
67.8 C
22.02min
-0.94 uV
843.2 ug
27.9 C
5.66min
0.02uV
55.00
41.25
27.50
13.75
0.00
TIME min
5.00
1.25
-2.50
-6.25
-10.00
DTA uV
170.0
130.0
90.0
50.0
10.0
TEMP C INITIAL
AS HEATED
4000.0
3200.0
2400.0
1900.0
1500.0
1100.0
850.00
650.00
450.00
WAVENUMBERS (CM-1)

AS HEATED
AS STORED UNDER DRIED CONDITIONS AT ROOM TEMPERATURE
WAVENUMBERS (CM-1)
4000.0
3200.0
2400.0
1900.0
1500.0
1100.0
850.00
650.00
450.00

5°
15°
25°
35°(2θ)

2 THETA
INTENSITY
5.00
7.00
9.00
11.00
13.00
15.00
17.00
19.00
21.00
23.00
25.00
27.00
29.00
31.00
33.00
35.00
0.00
16.00
32.00
48.00
64.00
80.00
96.00

5°
15°
25°
35°(2θ)

2 THETA
5.00
7.00
9.00
11.00
13.00
15.00
17.00
19.00
21.00
23.00
25.00
27.00
29.00
31.00
33.00
35.00
INTENSTY
0.00
16.00
32.00
48.00
64.00
80.00
96.00 b) 40°C 75%RH 1WEEK c) 40°C 100%RH 1WEEK

| X-Ray Spectrograph (PHILIPS PW 1730/10) | | |
|---|---|---|
| Date: 90/4/27 | No: | |
| Sample: Q-35 (V013D17) 40° 100%RH 1W | | mg |
| Filter: | Ni | |
| Monochromator: | graphite | |
| Voltage: | 40 | kV |
| Current: | 25 | mA |
| Count Full Scale: | 2000 | c/s |
| Time Constant: | 0.5 | sec |
| Scanning Speed: | 2 | °2θ/min |
| Scanning Angle: | 5° ~ 35° | |
| Chart Speed: | 2 | cm/min |
| Divergence Slit: | 1 | ° |
| Receiving Slit: | 0.2 | mm |
| Scattering Slit: | 1 | ° |
| Detector: | SC | |
| Remarks: | | |

40°C 100%RH 1WEEK
X-Ray Spectrograph
(PHILIPS PW 1730/10)
Date: 90/4/27 No.:
Sample: Q-35 V008B07
100%RH 1W mg
Filter: Ni
Monochromator: graphite
Voltage: 40 kV
Current: 25 mA
Count Full Scale: 2000 c/s
Time Constant: 0.5 sec
Scanning Speed: 2 °2θ/min
Scanning Angle: 5° ~ 35 °
Chart Speed: 2 cm/min
Divergence Slit: 1 °
Receiving Slit: 0.2 mm
Scattering Slit: 1 °
Detector: SC
Remarks:

a) POWDER BLENDED IN EtOH

| X-Ray Spectrograph (PHILIPS PW 1730/10) | | |
|---|---|---|
| Date: 90/4/26 No.: | | |
| Sample: Q-35 V013D17 Powder Blended In EtOH | | mg |
| Filter: | Ni | |
| Monochromator: | graphite | |
| Voltage: | 40 | kV |
| Current: | 30 | mA |
| Count Full Scale: | 1000 | c/s |
| Time Constant: | 0.5 | sec |
| Scanning Speed: | 2 | °2θ/min |
| Scanning Angle: | 5° ~ 35° | |
| Chart Speed: | 2 | cm/min |
| Divergence Slit: | 1 | ° |
| Receiving Slit: | 0.2 | mm |
| Scattering Slit: | 1 | ° |
| Detector: | SC | |
| Remarks: Transparent Cell | | |

b) POWDER BLENDED IN 50% EtOH
X-Ray Spectrograph
(PHILIPS PW 1730/10)
Date: 90/4/26 No.:
Sample: Q-35 V013D17
Powder Blended in 50% EtOH
Filter: Ni
Monochromator: graphite
Voltage: 40 kV
Current: 30 mA
Count Full Scale: 1000 c/s
Time Constant: 0.5 sec
Scanning Speed: 2 °2θ/min
Scanning Angle: 5° ~ 35 °
Chart Speed: 2 cm/min
Divergence Slit: 1 °
Receiving Slit: 0.2 mm
Scattering Slit: 1 °
Detector: SC
Remarks: Transparent Cell c) POWDER BLENDED IN $H_2O$ a) POWER BLENDED IN EtOH b) POWDER BLENDED IN 50% EtOH
X-Ray Spectrograph
(PHILIPS PW1730/10)
Date: 90/4/26 No:
Sample: Q-35 V008B17
Powder Blended in 50% EtOH mg
Filter: Ni
Monochromator: graphite
Voltage: 40 kV
Current: 25 mA
Count Full Scale: 2000 c/s
Time Constant: 0.5 sec
Scanning Speed: 2 °2θ/min
Scanning Angle: 5° ~ 35 °
Chart Speed: 2 cm/min
Divergence Slit: 1 °
Receiving Slit: 0.2 mm
Scattering Slit: 1 °
Detector: SC
Remarks: Transparent Cell c) POWDER BLENDED IN $H_2O$

| X-Ray Spectrograph (PHILIPS PW 1730/10) | |
|---|---|
| Date: 90/4/26 | No.: |
| Sample: Q-35 V008B07 Powder Blended in $H_2O$ | mg |
| Filter: | Ni |
| Monochromator: | graphite |
| Voltage: | 40 kV |
| Current: | 25 mA |
| Count Full Scale: | 2000 c/s |
| Time Constant: | 0.5 sec |
| Scanning Speed: | 2 °2θ/min |
| Scanning Angle: | 5° ~ 35° |
| Chart Speed: | 2 cm/min |
| Divergence Slit: | 1 ° |
| Receiving Slit: | 0.2 mm |
| Scattering Slit: | 1 ° |
| Detector: | SC |
| Remarks: Transparent Cell | |

QUINOLONE CARBOXYLIC ACID DERIVATIVES IN CRYSTALLINE HYDRATE FORM

This application is a 371 of PCT/JP 93/00109, filed 29 Jan. 1993.

TECHNICAL FIELD

This invention relates to 1-cyclopropyl-6-fluoro-1,4-dihydro-8-methoxy-7-(3-methylaminopiperidin-1-yl)-4-oxoquinoline-3-carboxylic acid dihydrate that is useful as an antimicrobial agent and which has satisfactory stability.

BACKGROUND ART

The official gazette of Japanese Patent Public Disclosure (KOKAI) No. Hei 3-95177 discloses 1-cyclopropyl-6-fluoro-1,4-dihydro-8-methoxy-7-(3-methylaminopiperidin-1-yl)-4-oxoquinoline-3-carboxylic acid (hereunder designated "Q-35"). The official gazette further teaches that Q-35 is the product of recrystallization from acetonitrile and that it has satisfactory antimicrobial activity.

However, as continued research was undertaken to commercialize it as a medicine, the Q-35 recrystallized from acetonitrile turned out to have only low stability due to the drawback that its weight would increase with increasing humidity. Under the circumstances, it was impossible to administer the Q-35 in well-defined doses and this, combined with other problems of the Q-35 made it difficult to develop said compound as a medicine. Hence, there was the need to develop a technique by which stable Q-35 could be produced even under humid conditions.

DISCLOSURE OF INVENTION

The present inventors conducted intensive studies with a view to eliminating the above-described drawback of Q-35 recrystallized from acetonitrile. As a result, they found that Q-35 had four crystal forms, a crystal with a variable water content (which is hereunder referred to as "crystal III" or "type III crystal"), a monohydrate crystal (which is hereunder referred to as "crystal II" or "type II crystal"), a dihydrate crystal (which is hereunder referred to as "crystal I" or "type I crystal"), and an anhydride crystal, and that the specific type of crystal to be produced is determined by the type of solvent used for recrystallization. As a result of closer studies conducted on the physical properties of the respective crystal forms, the inventors found the following: the Q-35 recrystallized from acetonitrile was a type III crystal; type I crystal, namely, the dihydrate of Q-35, was the most stable under humid conditions and, although it turned to an anhydride under drying or heating conditions, it reverted to the dihydrate when left to stand. The present invention has been accomplished on the basis of this finding. Stated briefly, the invention relates to a 1-cyclopropyl-6-fluoro-1,4-dihydro-8-methoxy-7-(3-methylaminopiperidin-1-yl)-4-oxoquinoline-3-carboxylic acid dihydrate having the following formula:

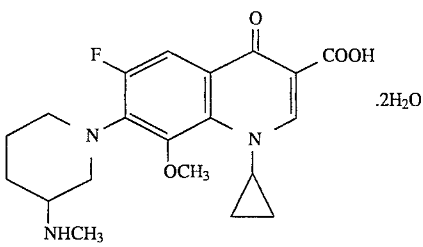

BEST MODE FOR CARRYING OUT THE INVENTION

Figure 1:
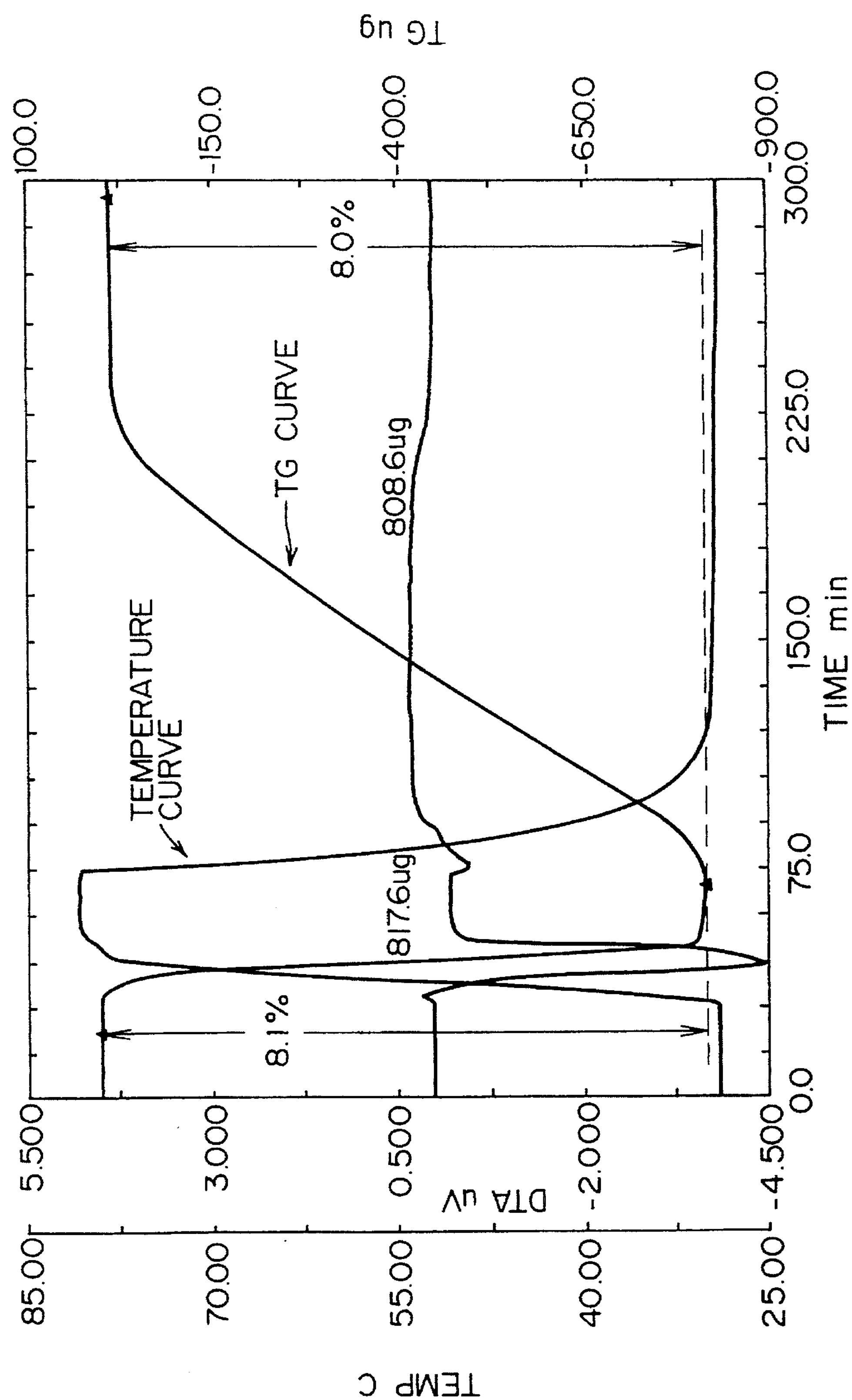
FIG. 1 shows the weight change of type I crystal of Q-35 when it was stored under atmospheric conditions after heating.

Q-35 can be synthesized either by a method (process I) in which 1-cyclopropyl-6,7-difluoro-1,4-dihydro-4-oxo-3-quinolinecarboxylic acid (DFQ) is condensed directly with 3-methylaminopiperidine (3-MAP) or by a method (process II) in which DFQ-Et is reacted with $HBF_4$ to form $DFQ-BF_2$ chelate ($DFQ-BF_2$), which is condensed with 3-MAP to form Q-35 $BF_2$ chelate ($Q-35-BF_2$), which is thereafter hydrolyzed with $Et_3N$ or an aqueous solution of NaOH or the like to yield Q-35. Process II achieves a higher yield and, hence, is suitable for large-scale synthesis. The reaction routes of processes I and II are as following:

Process I:

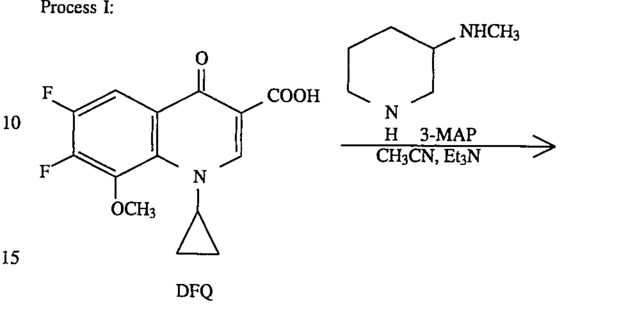

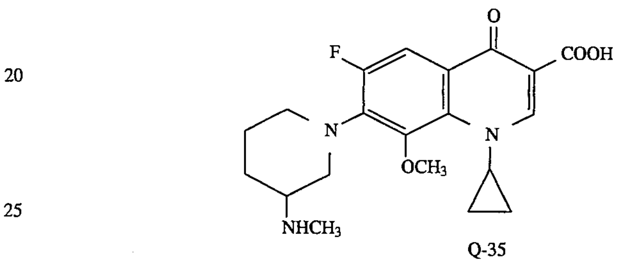

Process II:

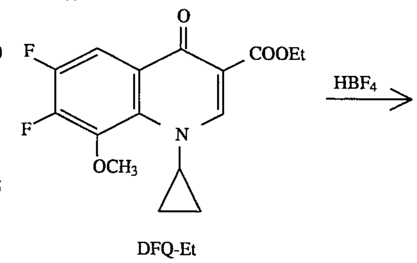

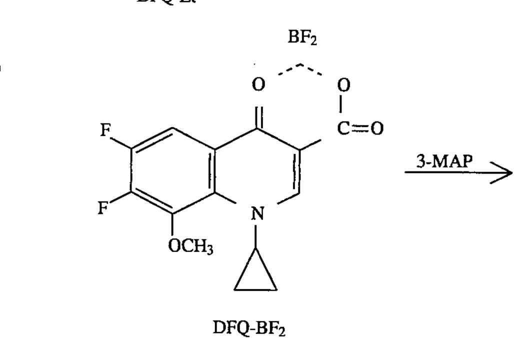

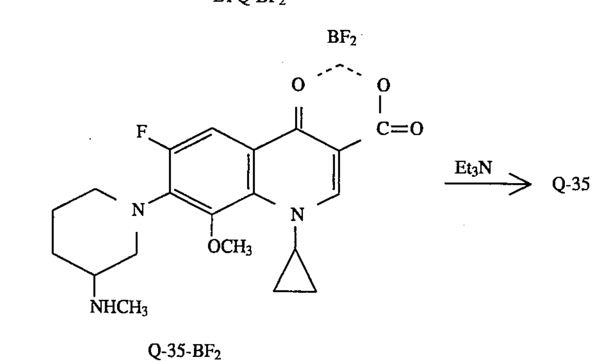

For purification, the Q-35 obtained by process I or II is heated for refluxing and drying in a solvent, then purified with a purifying solvent. Which of the crystal forms described hereinabove will be yielded in this case depends on the purifying solvent used. If acetonitrile-water is used, either type III crystal or type II crystal is obtained; with methanol, type II crystal is obtained; and with ethanol-water (1:1), type I crystal is obtained. The present inventors studied under what conditions these three kinds of crystal forms would be obtained and discovered the following: type III crystal yielded when the formation of a complete solution in ethanol or acetonitrile was followed by distilling off the solvent under vacuum; type II crystal yielded when the formation of a suspension in methanol was followed by heating under reflux; and type I crystal yielded when the formation of a suspension in ethanol-water (1:1) was followed by heating under reflux.

Crystal II transforms to crystal I upon wetting and blending (in 50% ethanol or water). On the other hand, crystal I shifts to crystal II upon heating under reflux in the presence of methanol but no crystal transformation occurs upon wetting and blending (in 50% ethanol or water). The inventors further verified that upon drying, crystal II and crystal I were deprived of the water of crystallization to become anhydrides but that upon standing in air, the anhydrides reverted to their respective hydrate forms.

Shown below are examples of the production of the compound of the present invention but it should be understood that the invention is in no way limited to those examples.

EXAMPLE 1

DFQ-$BF_2$ ester (3.4 g), 3-methylaminopiperidine.2HCl (3-MAP.2HCl; 2.3 g) and triethylamine (4.5 g) were added to methylene chloride (18 ml) and the mixture was heated under reflux for 3 h. After distilling off the methylene chloride under vacuum, a solution consisting of NaOH (2.5 g) and water (20 ml) was added and reaction was carried out at 80° C. for 1.5 h. After cooling, the reaction solution was adjusted to a pH of 8–9 with 6N HCl for crystallization. The precipitating crystal was centrifuged to give a wet powder of crude Q-35 in an amount of 4.2 g (3.2 g on a dry basis; yield, 83.0%).

Fumaric acid (3.5 g) was dissolved in a 90% aqueous methanol solution (102 ml). To the resulting solution, crude Q-35 was added in an amount of 9.4 g (on a dry basis). The solution was cooled and the precipitating crystal was centrifuged to give a wet powder of Q-35.fumarate in an amount of 12.1 g (11.0 g on a dry basis; yield, 90.1%).

NaOH (3.6 g) was dissolved in water (100 ml). To the resulting solution, Q-35.fumarate (11.0 g) was added and a solution was formed. After separating the insolubles by filtration, 6N HCl was added to adjust the pH to 8–9 for crystallization. The precipitating crystal was centrifuged and dried to produce type I crystal of purified Q-35 in an amount of 7.7 g (yield: 83.2%).

EXAMPLE 2

A 200-ml reaction vessel was charged with a 9.1% (w/w) MAP methanol solution (61.7 g, 49.3 mmol) and heated with warm (60° C.) water under vacuum to distill off about 55 ml of methanol. To the resulting concentrate residue, methylene chloride (65 ml) triethylamine (7.7 g, 75.8 mmol) and DFQ-$BF_2$ ester (13.0 g, 37.9 mmol) were added and the mixture was reflexed for 1 h. A solution formed gradually and it turned clear and yellow. The solvent in the reaction solution was distilled off under vacuum. To the concentrate residue, water (30 ml) and a 25% aqueous sodium hydroxide solution (39 g, 244 mmol) were added and hydrolysis was performed at 70° C. for 1 h (upon heating to about 50° C., the remaining solvent stated to distill off). After water-cooling the liquid hydrolysis mixture, its pH was adjusted to 8.5 with about 30 ml of 5.5N HCl (1/1) and heating was done at 60° C. for 30 min to promote crystallization. The liquid mixture was cooled to 25° C. and stirred for 1 h. Subsequently, the liquid mixture was loaded in a 24-in centrifuge for about 45 min to separate the crystal. The resulting crystal was washed with water (20 ml) and shaken out for 30 min to give a wet powder of crude Q-35 in an amount of 18.2 g (net: 13.8 g; yield, 94%).

A 200-ml reaction vessel was charged with ion exchanged water (100 ml), conc. HCl (4.3 ml, 47.3 mmol) and the wet powder of crude Q-35 (18.2 g; net=13.8 g (35.5 mmol)) to give a pH of 3–4. Two extractions were conducted, each with 30 ml of ethyl acetate. By heating with warm (70° C.) water under vacuum, the ethyl acetate dissolved in aqueous layer was distilled off (ca. 1.5 h). The aqueous layer was rendered acidic by addition of HCl (2 ml) and the resulting small amount of insolubles were separated by filtration. After being adjusted to a pH of 8.5 with about 8 ml of a solution of sodium hydroxide in water (3 g in 10 ml), the filtrate was heated at 60° C. for 30 min to promote crystallization. After the end of heating, the solution was cooled to 25° C. and stirred for 1 h. Subsequently, the filtrate was loaded in a 24-in centrifuge for about 30 min to separate the crystal. The resulting crystal was washed with ion-exchanged water (20 ml) and shaken out for 30 min to produce 13.7 g of the crystal.

A 200-ml reaction vessel was charged with ethanol (80 ml), water (80 ml) and the crystal (13.7 g) and the mixture was heated at 70° C. and stirred for 30 min as a suspension. The resulting liquid mixture was cooled to 25° C. and stirred for 1 h, followed by loading in a 24-in centrifuge for about 30 min to separate the crystal. The resulting crystal was washed with ion-exchanged water (20 ml) and shaken out for 30 min to produce a wet powder of Q-35. Using a through-flow dryer, the wet powder was dried at 60° C. for 2 h, then aerated at room temperature for 2 h to produce type I crystal of Q-35 in an amount of 10.1 g (yield, 73%).

Using the thus obtained type I crystal of Q-35, the following experiments were conducted in order to unravel its structure, as well as the behavior of the bimolecular water of crystallization.

EXPERIMENTS

1) Samples

As samples for infrared absorption spectroscopy, powder X-ray diffraction and thermal analyses, those which were produced by the methods of the Examples were used. As samples for single-crystal X-ray analysis, those which were prepared by the method described within the following parentheses were used. (Crystal for single-crystal X-ray analysis: Absolute ethanol (450 ml) was added to type I crystal of Q-35 (8.10 g) prepared by the methods of Examples 1 and 2 and the mixture was heated at 75° C. for 30 min to filter it while hot. After being left to stand at room temperature, the filtrate was further filtered by means of suction to produce a crystal (ca. 5.95 g). Water (300 ml) was added to the crystal and the mixture was heated at 95° C. for 5 min; after standing at room temperature, the mixture was filtered by means of suction and the filtrate was left to stand at room temperature to yield a crystal.)

2) Apparatus Used

TG/DTA: TG/DTA 200 of Seiko Denshi K.K.

DSC: DSC 210 of Seiko Denshi K.K.

Infrared spectrophotometer: 20 DXB of Nicolet

Powder X-ray diffractometer: PW 1730/10 of Phillips

Single-crystal X-ray diffractometer: CAD4 of Enraf-Nonius

3) Experimental Methods (1) Thermal Analyses

① Heating and Cooling Experiment (TG)

About 10 mg of a sample (being a powder, the sample need not be pulverized) was heated from room temperature up to 80° C. at a rate of 5° C/min, held at 80° C. for 30 min and thereafter cooled to room temperature. The changes that occurred in the weight of the sample as a result of its heating and cooling were examined. To avoid its drying effect, $N_2$ gas was not allowed to flow during the measurement (relative humidity in the room: 40–50 % R.H.)

② Experiment Under Exposure to an Anhydrous Atmosphere at Room Temperature Followed by Standing Under Atmospheric Condition (TG)

About 10 mg of a sample (not pulverized) was left to stand in an anhydrous atmosphere at room temperature with $N_2$ gas being allowed to flow at 200 ml/min and the resulting changes in the weight of the sample were examined. When there was no longer a change in the sample's weight, the supply of $N_2$ gas was stopped to create atmospheric conditions (relative humidity in the room: 40–50% R.H.), in which the changes in the sample's weight were examined again.

③ Experiment for Storage at Low Humidity (6% R.H.) (TG)

About 10 mg of a sample (not pulverized) was heated to dehydrate in an anhydrous atmosphere under a $N_2$ gas flow. Thereafter, air* humidified to 6% R.H. was allowed to flow at 200 ml/min at room temperature and the resulting changes in sample's weight were examined.

* Saturated NaOH solution was stored in a desiccator and air humidified to 6% R.H. with NaOH was circulated.

④ Heating Experiment and the Calculation of Activation Energy (TG/DTA)

About 10 mg of a sample (not pulverized) was heated from room temperature up to 170° C. at rates of 2°, 3° and 5° C./min. The resulting changes in sample's weight and the thermal changes that accompanied were examined and the activation energy was determined from the weight changes by the Ozawa method. To avoid its drying effect, $N_2$ gas was not allowed to flow during the measurement (relative humidity in the room: 40–50% R.H.)

⑤ Heating Experiment (DSC)

About 10 mg of a sample (not pulverized) was subjected to measurements, with the sample pan being kept open with no crimps applied in order to avoid pressurization by steam. During the measurement, $N_2$ gas was allowed to flow at 20 ml/min and when thermal stability was reached (in about 3 min), the sample was heated from room temperature up to 170° C. at a rate of 3° C./min and the resulting thermal changes were examined.

(2) Infrared Absorption Spectra

① Heating (80° C.) Followed by Standing in an Indoor Atmosphere

A sample was mixed and diluted with KBr to a concentration of 5%, heated in a heating cell for powder X-ray diffraction and subjected to a measurement by the method of diffuse reflection analysis (DRA); the number of scans, 2048; gain, 16. Both the heating experiment and the experiment in an indoor atmosphere were conducted with the sample chamber being kept open to avoid the effect of drying air (relative humidity in the room: 20–30% R.H.) and the same procedure was followed to perform measurements on the reference. In the experiment in an anhydrous atmosphere, the sample chamber was closed and the anhydrous atmosphere was created by supplying drying air and the same procedure was followed to perform measurements on the reference.

② Experiment in an Anhydrous Atmosphere at Room Temperature, Followed by Experiment in an Indoor Atmosphere A sample was mixed and diluted with KBr to a concentration of 5% and subjected to measurements by the method of diffusive reflection analysis (DRA); the number of scans, 1024; gain, 8. A convenient DRA cell was used for the measurements. The experiment under dried conditions was conducted with the sample chamber being closed under a drying air flow, and the same procedure was followed to perform measurements on the reference. In the experiment under atmospheric conditions, the sample chamber was kept open (relative humidity in the room: 20–30% R.H.) and the same procedure was followed to perform measurements on the reference.

(3) Powder X-ray Diffraction Spectra

1 Heating (80° C.) Followed by Standing Under Atmospheric Conditions

A sample was pulverized and heated up to 80° C. in a heating cell at a rate of 5° C./min; thereafter, $N_2$ gas was allowed to flow to create an anhydrous atmosphere, followed by cooling to room temperature. Subsequently, the supply of $N_2$ gas was stopped to create an indoor atmosphere for measurement (relative humidity in the room: 60–70% R.H.)

2 Exposure to an Anhydrous Atmosphere at Room Temperature, Followed by Standing in an Indoor Atmosphere A sample was pulverized and placed in a heating cell, through which $N_2$ gas was allowed to flow to create an anhydrous atmosphere and measurements were performed at given time intervals. Thereafter, the supply of $N_2$ gas was stopped to create atmospheric conditions and measurements were conducted (relative humidity in the room: 60–70%).

(4) Single-crystal X-ray Analysis

After measurements (R.H.: 60–70% at room temperature), $N_2$ gas was allowed to flow to create an anhydrous atmosphere and measurements were conducted. Thereafter, the sample was stored again under atmospheric conditions and measurements were conducted.

4) Experimental Results and Discussion (1) Analyzing the Behavior of the Water of Crystallization by Thermal Analyses Type I crystal (dihydrate) of Q-35 was heated from room temperature up to 80° C. (without flowing $N_2$ gas so that it would not cause any adverse effects) in the TG method; as a result, the weight of the crystal decreased with the increasing temperature and the ultimate weight loss was about 8.1%. Since the theoretical value of the water content in type I crystal of Q-35 is 8.47%, the weight loss is estimated to correspond to the water of crystallization. In other words, the sample after weight loss due to heating would be a dehydrated anhydride. In the subsequent cooling phase, the weight of the sample started to increase as soon as its temperature was lowered and the initial weight was restored in about 150 min (FIG. 1). From these facts, it was estimated that the two molecules of the water of crystallization in type I crystal of Q-35 were eliminated upon heating but that the crystal incorporated the moisture of air at room temperature to become stabilized again in the state of bimolecular water of crystallization. Verification of the fact that the change in the sample's weight was due to the water of crystallization was made in "(2) Structural changes".

Figure 2:
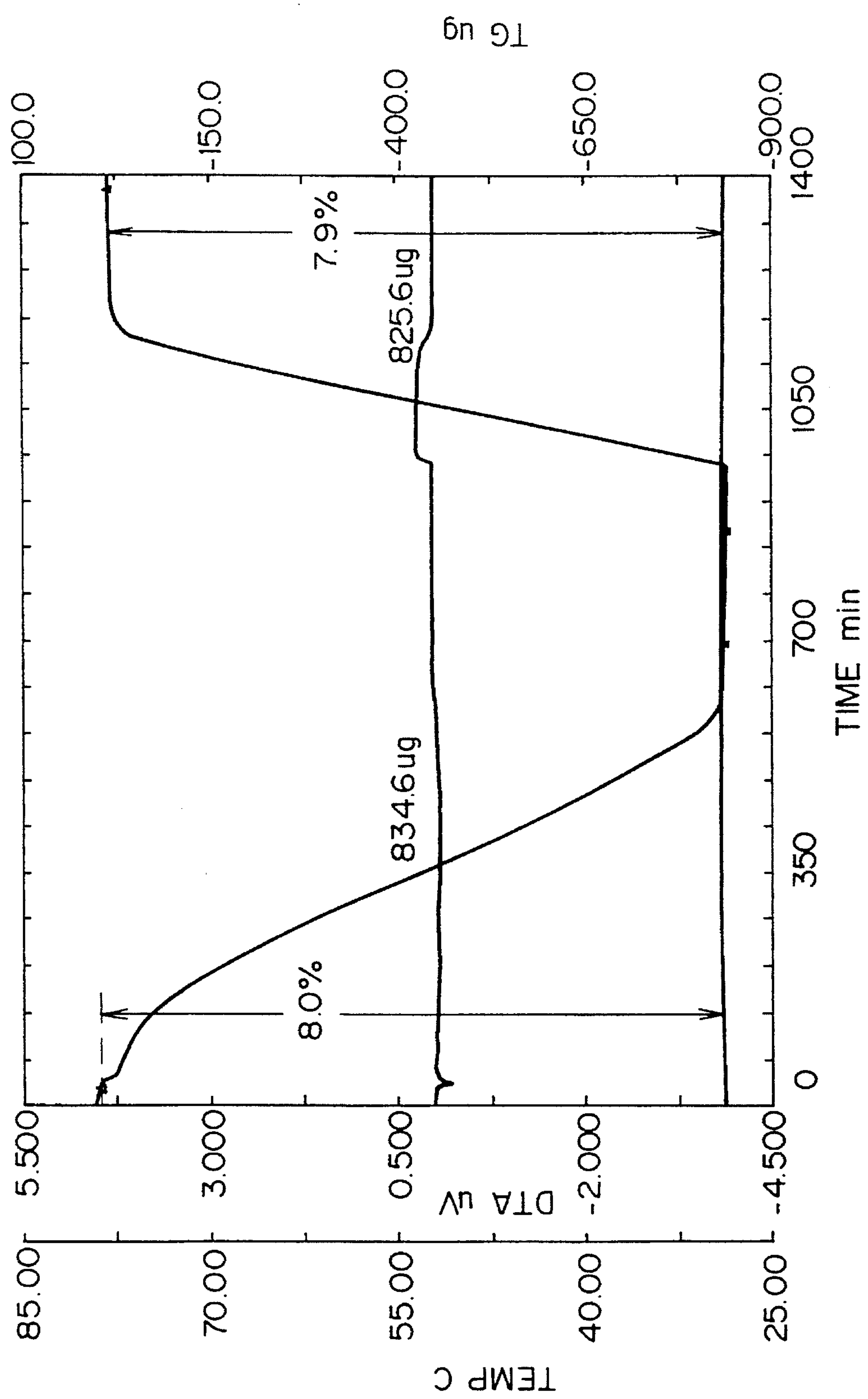
FIG. 2 shows the weight change of type I crystal of Q-35 when it was first stored under dried conditions at room temperature, then stored under atmospheric conditions.

Another sample of type I crystal of Q-35 was stored in an anhydrous atmosphere at room temperature and about 8.0% weight loss occurred in about 700 min. When the sample was subsequently stored under atmospheric conditions, its weight increased rapidly and reverted to the same level as the initial in about 150 min (FIG. 2). This indicates that the water of crystallization in type I crystal of Q-35 is eliminated not only by heating but that there is also a good chance for the water of crystallization to be eliminated under dried conditions at room temperature.

Figure 3:
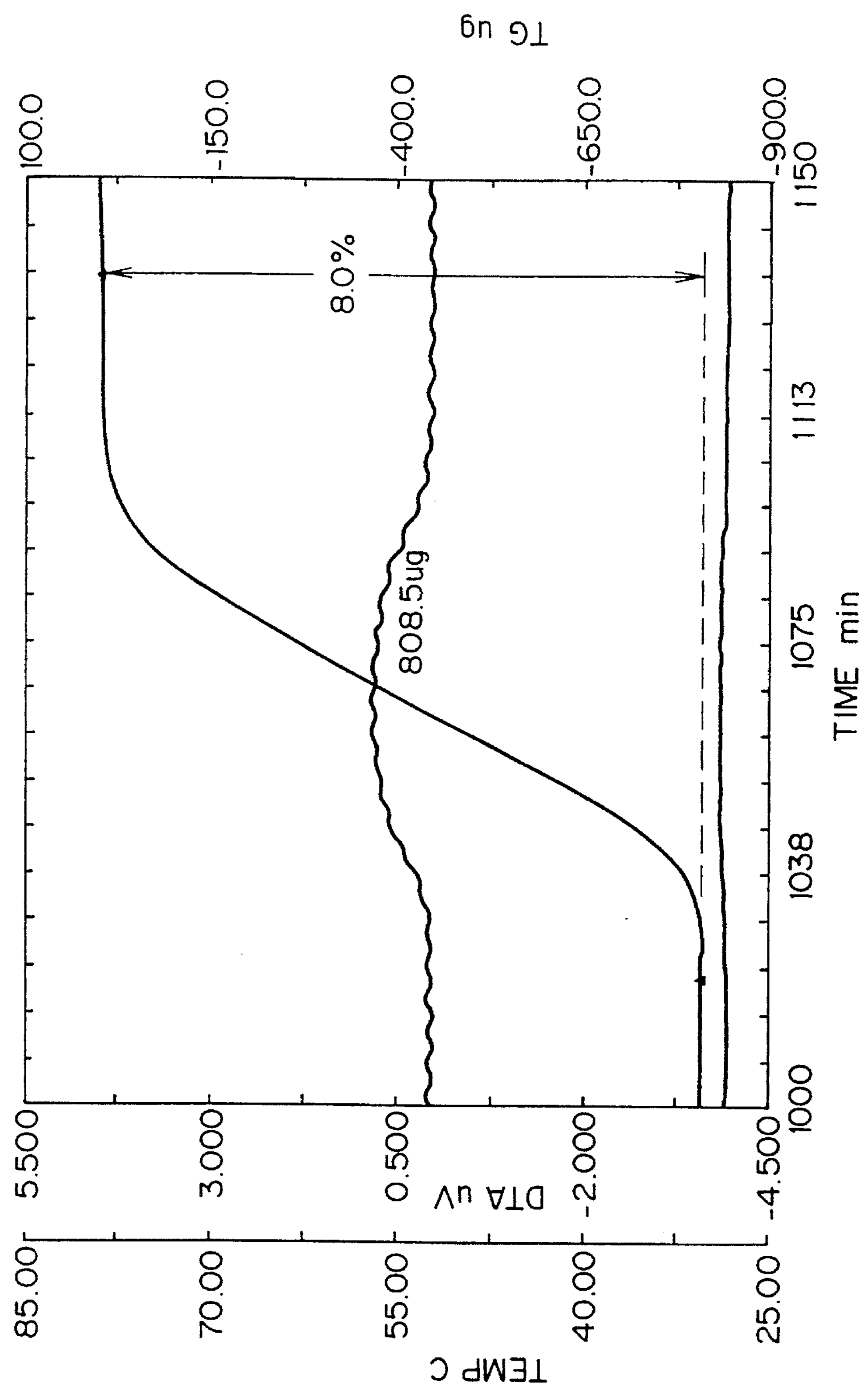
FIG. 3 shows the weight change of dehydrated type I crystal of Q-35 when it was stored under dried conditions (6% R.H.) at room temperature.

Thus it was verified that dehydration of two molecules also occurred during storage under dried conditions at room temperature and that complete reabsorption of water was achieved by the dehydrate when it was stored under atmospheric conditions at 40–50% R.H. One may then ask what will be the state in which type I crystal of Q-35 exists at low humidity in the presence of a very small amount of water. Two of the possibilities that can be assumed are as follows: 1) the bimolecular water of crystallization is incorporated into the crystal even at low humidity and the crystal exists as a dihydrate; or 2) at humidities lower than a certain point, the crystal exists in an intermediate state such as anhydride or monohydrate. To check which of the possibilities was real, the inventors first dehydrated the crystal, then allowed humidified air (6% R.H.) to flow at room temperature and measured the resulting change in weight. It was verified that the crystal absorbed water rapidly in spite of the low humidity of the atmosphere and reverted to the weight of the dihydrate in about 60 min with no intermediate state such as monohydrate being observed in the process of water absorption (FIG. 3). The rate of water absorption was faster at 6% R.H. than under atmospheric conditions probably due to the difference in air flow during measurements.

Figure 4:
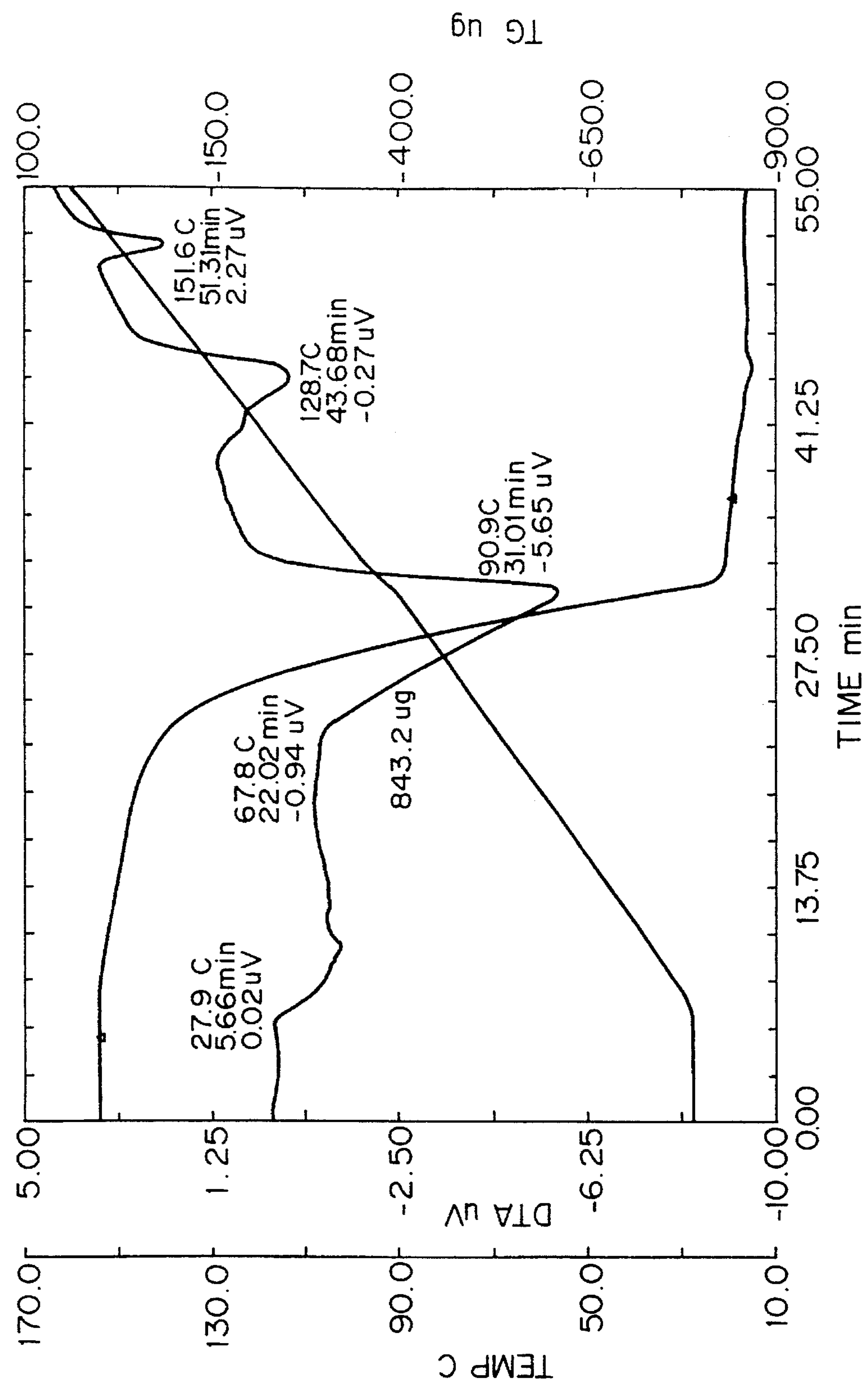
FIG. 4 shows TG and DTA curves obtained when type I crystal of Q-35 was heated from room temperature up to 170° C. at a rate of 3° C./min.
Figure 5:
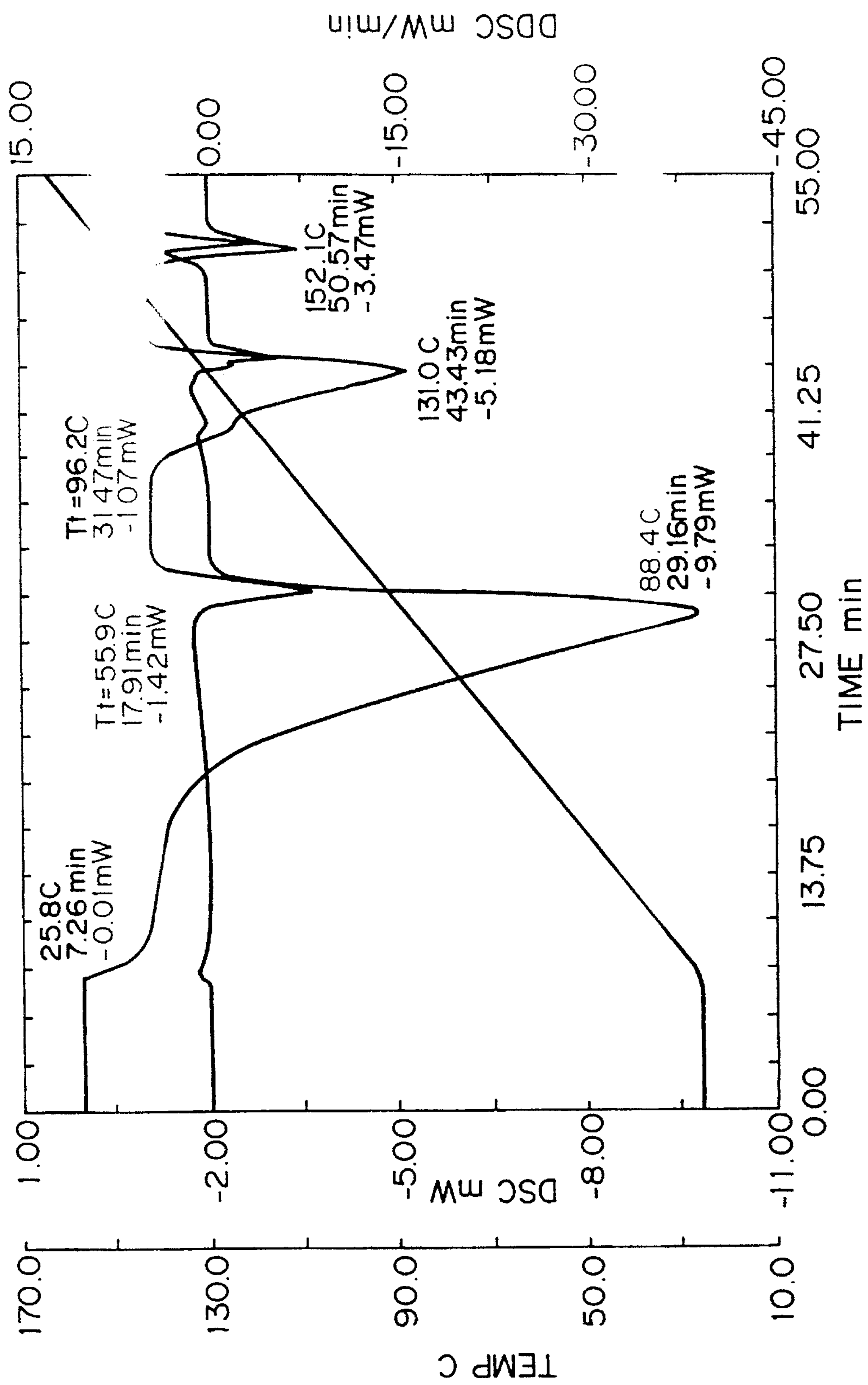
FIG. 5 shows a DSC curve obtained when type I crystal of Q-35 was heated from room temperature up to 170° C. at a rate of 3° C./min.

In the case of dehydration by heating, the TG curve (FIG. 4) was such that as soon as temperature rose, a gradual weight loss occurred, followed by a noticeable abrupt weight loss until a plateau was reached. In the meantime, the DTA curve had two noticeable peaks in the process of dehydration, one being a mild peak of DTA during the gradual weight loss in TG and the other being a large peak of DTA during the abrupt weight loss in TG. This may be explained as follows: of the two kinds of water that are present, the easy to eliminate water evaporates first and the difficult to eliminate water evaporates thereafter and these two reaction stages combine together. As on the DTA curve, two peaks were observed on the DSC curve in the process of dehydration (FIG. 5). On the other hand, the TG curve (FIG. 2) as obtained with $N_2$ gas being allowed to flow at room temperature (under dried conditions at room temperature) was such that a moderate weight loss occurred immediately after $N_2$ gas was allowed to flow, followed by a gradual weight loss which, in turn, was followed by an abrupt weight loss until a plateau was reached. In this case, the water in the surface of the sample evaporated first and subsequently, as in the case of heating, the easy to eliminate water evaporated first and the difficult to eliminate water evaporated thereafter and these two reaction stages would have combined together.

(2) Structural Changes

① Infrared Absorption Spectroscopy i) Heating (80° C.) Followed by Standing in an Indoor Atmosphere It was verified by the TG method that type I crystal of Q-35, when heated (80° C.), experienced a weight loss corresponding to the theoretical value for the water of crystallization and that subsequent cooling to room temperature caused reversion to the initial weight. Since the amount of the change in weight agreed with the theoretical value for the water of crystallization, the inventors estimated that the weight change of interest was due to the desorption of the two molecules of the water of crystallization and verified this assumption by infrared absorption spectroscopy.

Figure 6:
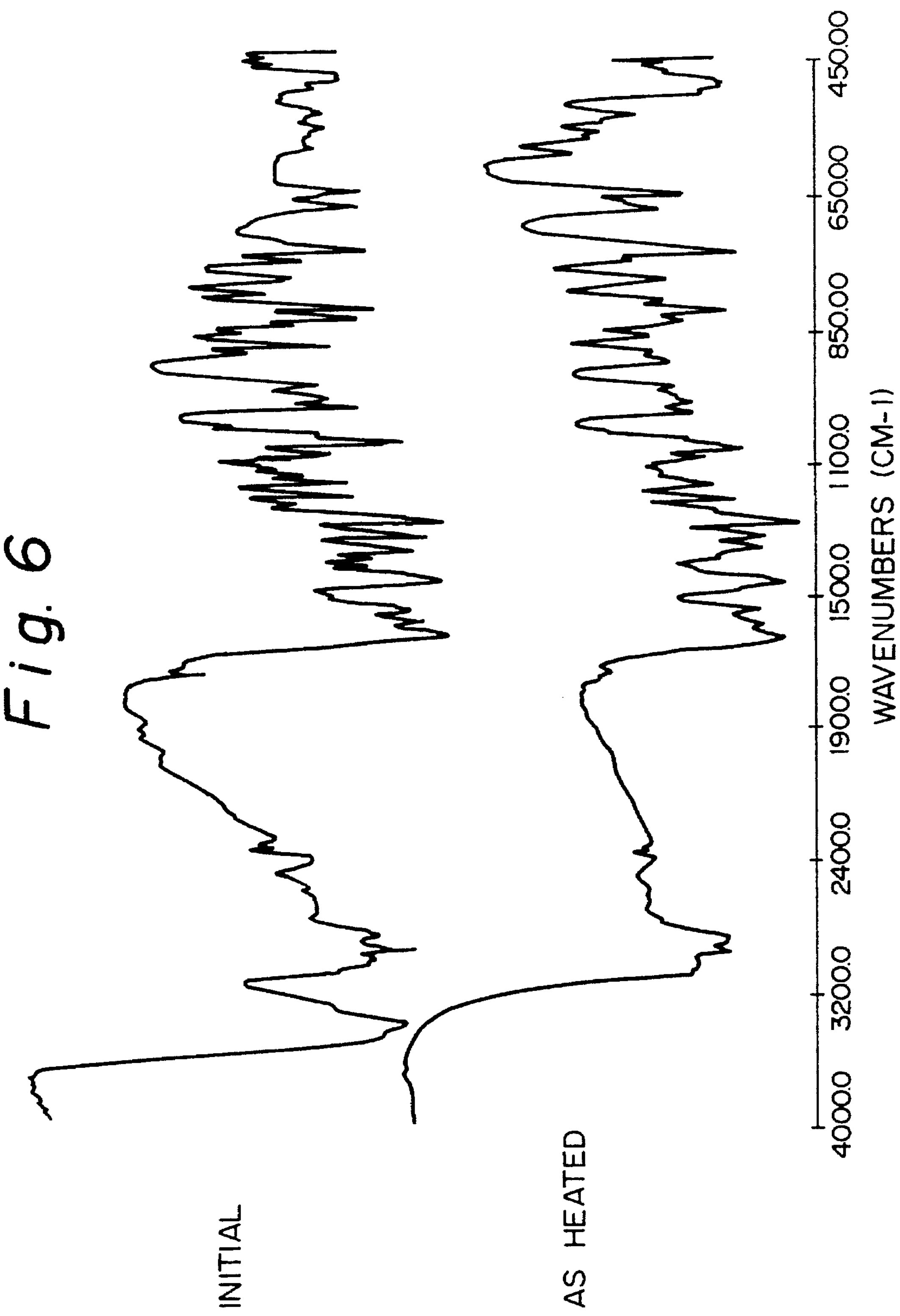
FIG. 6 shows infrared absorption spectra for type I crystal of Q-35 in both the initial and heated states.
Figure 7:
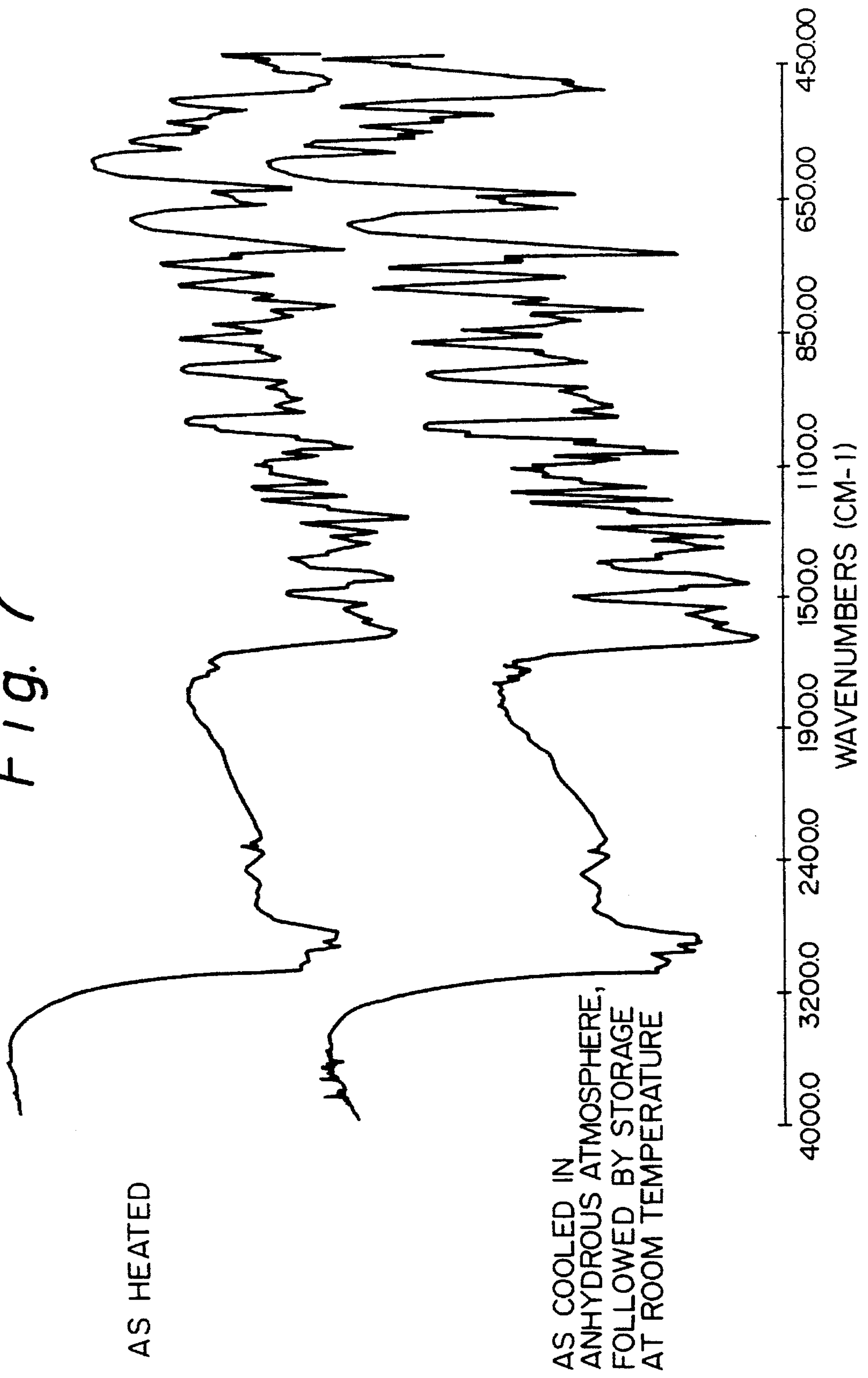
FIG. 7 shows infrared absorption spectra for type I crystal of Q-35 both in the heated state and after cooling in an anhydrous atmosphere followed by storage at room temperature.
Figure 8:
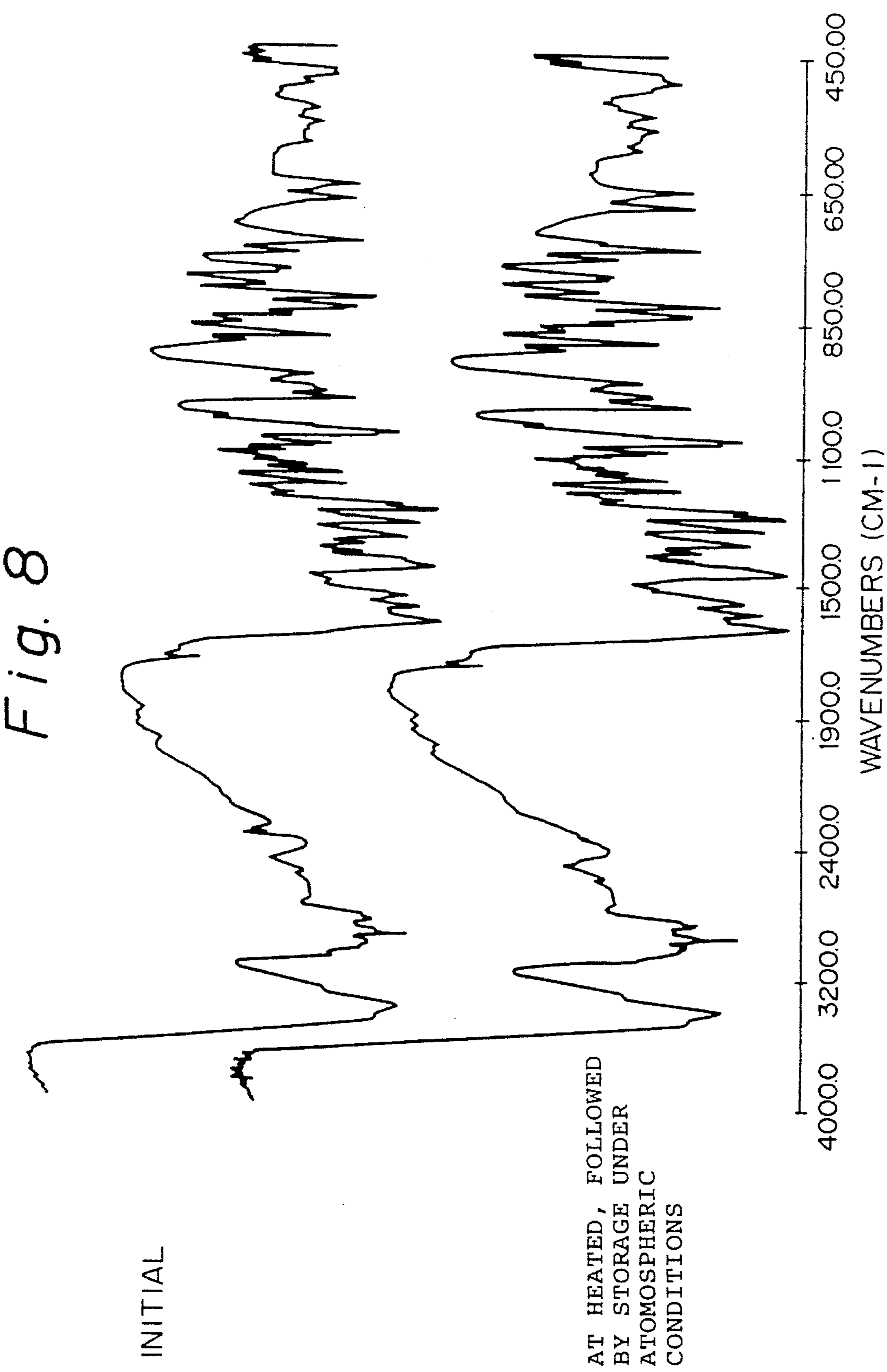
FIG. 8 shows infrared absorption spectra for type I crystal of Q-35 both in the initial state and after heating followed by storage under atmospheric conditions.

The spectrum for the initial state showed a strong $\nu_{O-H}$ ($H_2O$) peak due to the water of crystallization (FIG. 6). Upon heating (80° C.), the absorption of $\nu_{O-H}$ ($H_2O$) disappeared completely, verifying that the crystal dehydrated at 80° C. to become an anhydride (FIG. 6). The spectrum also changed at smaller wave numbers than $\nu_{C=O}$ (carboxylate and ketone: 1622 $cm^{-1}$), suggesting that a certain change occurred as a result of dehydration. The water of crystallization was bound to the oxygen in carboxylate (Q-35 assuming the betaine structure) and the $\nu_{C=O}$ absorption by carboxylate (at 1622 and 1459 $cm^{-1}$) showed slight changes in the shape of peaks. Subsequently, the crystal was cooled under dried conditions and stored at room temperature but there was no noticeable absorption of $\nu_{O-H}$ ($H_2O$) and the spectrum agreed with that obtained after heating, showing that the crystal remained in a dehydrated state (FIG. 7). However, upon storage under atmospheric conditions, absorption of $\nu_{O-H}$ ($H_2O$) comparable to the one observed in the initial state occurred in about 24 h and the other peaks were in complete agreement with those in the initial spectrum, showing that the crystal assumed the same molecular structure of dihydrate as in the initial state (FIG. 8), whereby it was verified that the dehydrate incorporated water in the presence of water at room temperature. These results show the following: upon heating, type I crystal of Q-35 had the water of crystallization eliminated to become an anhydride but when stored under atmospheric conditions, the crystal absorbed water to revert to the same molecular structure of dihydrate as in the initial state.

ii) Exposure to an Anhydrous Atmosphere at Room Temperature, Followed by Standing Under Atmospheric Conditions It was verified by the TG method that as in heating, exposure to an anhydrous atmosphere at room temperature caused a weight loss corresponding to the theoretical value for the water of crystallization and that subsequent standing under atmospheric conditions caused reversion to the initial weight. An infrared absorption spectrum verified that the weight loss due to heating was caused by dehydration. Other infrared absorption spectra were examined to confirm that the weight changes during exposure to an anhydrous atmosphere at room temperature were due to water and to check whether the dehydrate obtained by heating had a different molecular structure from the dehydrate obtained by exposure to an anhydrous atmosphere at room temperature.

Figure 9:
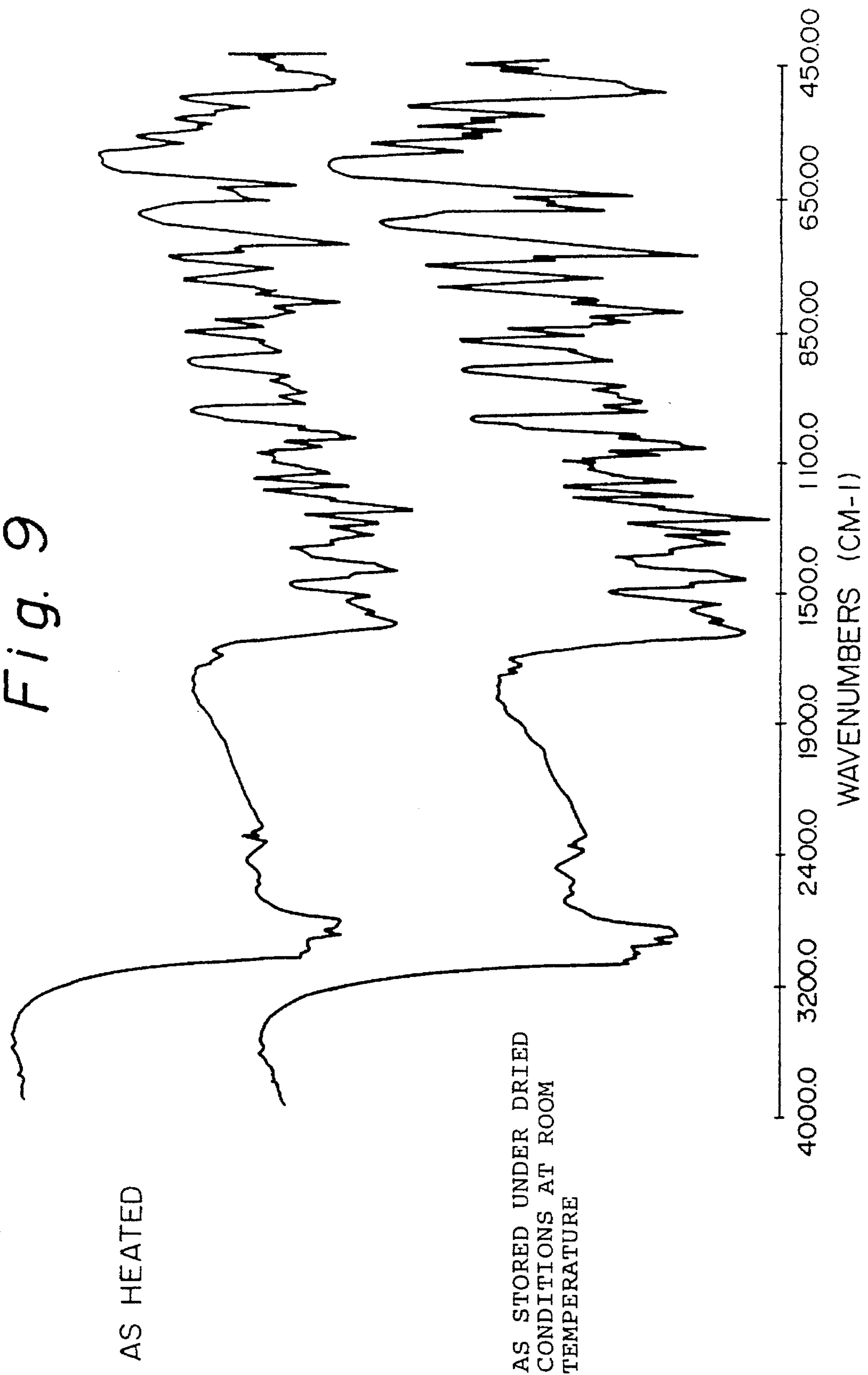
FIG. 9 shows infrared absorption spectra for type I crystal of Q-35 both in the heated state and after storage in an anhydrous atmosphere at room temperature.
Figure 10:
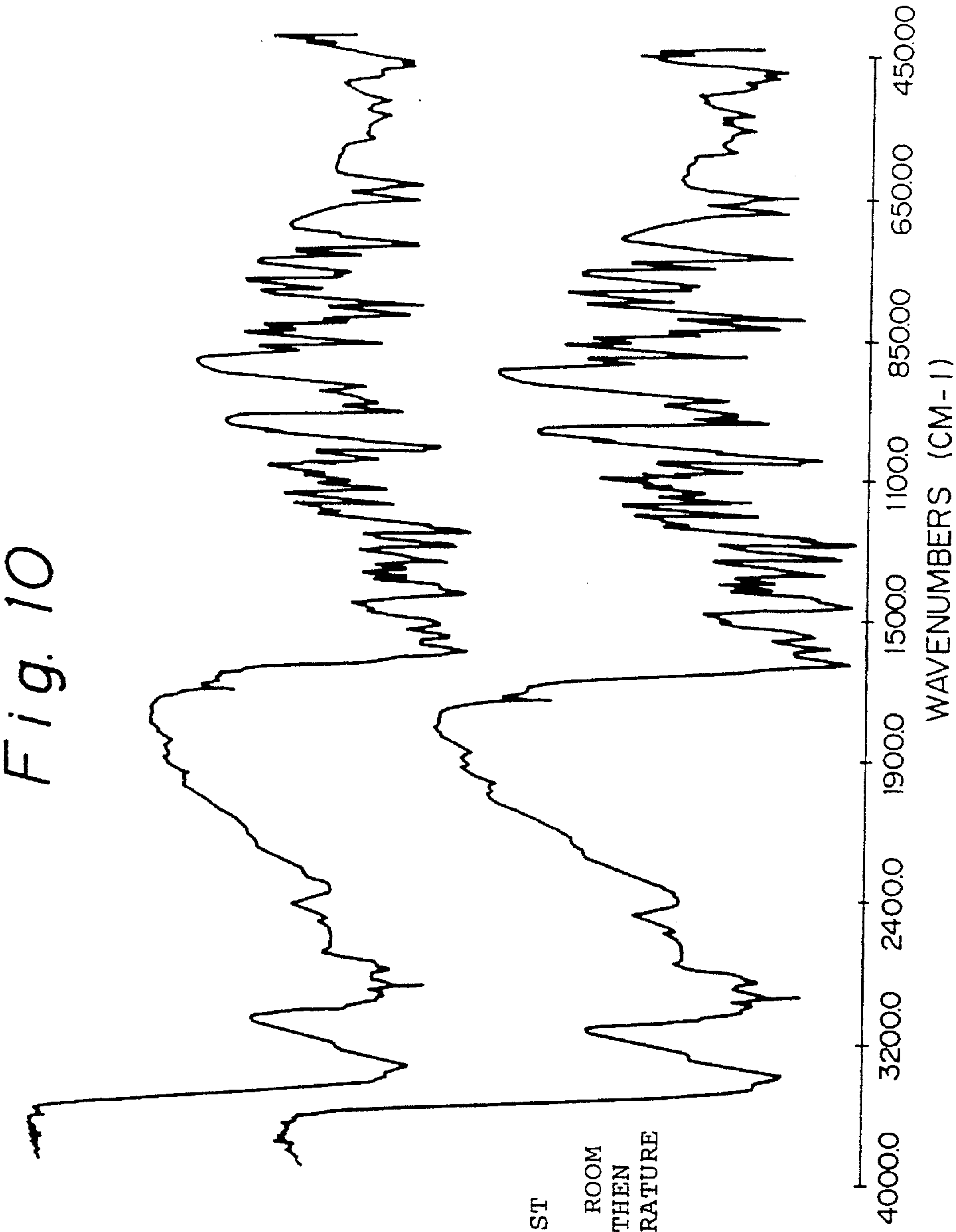
FIG. 10 shows infrared absorption spectra for type I crystal of Q-35 both in the initial state and after storage in an anhydrous state at room temperature followed by storage under atmospheric conditions.

Upon storage under atmospheric conditions, the absorption of $\nu_{O-H}$ ($H_2O$) disappeared as in heating and the resulting spectrum agreed completely with that obtained upon heating (FIG. 9); this indicated that merely by storing it under dried conditions at room temperature, the crystal was dehydrated to become an anhydride, which took on the same molecular structure as that obtained by heating. Upon subsequent storage under atmospheric conditions, the absorption of $\nu_{O-H}$ ($H_2O$) comparable to that obtained in the initial state was observed as in heating and the resulting spectrum agreed with the initial one, verifying that the crystal assumed the same molecular structure of dihydride as in the initial state (FIG. 10). It was therefore verified that upon storage under dried conditions at room temperature, the crystal was dehydrated to become an anhydride, that the dehydrated anhydride had the same molecular structure as the dehydrated anhydride that was formed by heating, and that upon subsequent storage under atmospheric conditions, the crystal reverted to the same molecular structure of dihydride as in the initial state.

Measurements of Infrared absorption spectra thus verified the following: type I crystal of Q-35 was dehydrated to yield an anhydride both under heating (80° C.) and upon exposure to an anhydrous atmosphere at room temperature; the dehydrated product had the same molecular structure irrespective of the drying conditions; and upon storage in a room temperature atmosphere, the crystal absorbed moisture again to revert the same molecular structure of dihydrate as in the initial state, indicating the reversible nature of water desorption.

(2) Powder X-ray Diffraction i) Heating (80° C.) Followed by Standing Under Atmospheric Conditions It was verified by infrared absorption spectra that dehydration occurred both under heating and upon exposure to an anhydrous atmosphere at room temperature but that water returned upon storage under atmospheric conditions. Under the circumstances, the changes that occurred in the crystal structure as a result of dehydration were examined by powder X-ray diffraction.

Figure 11:
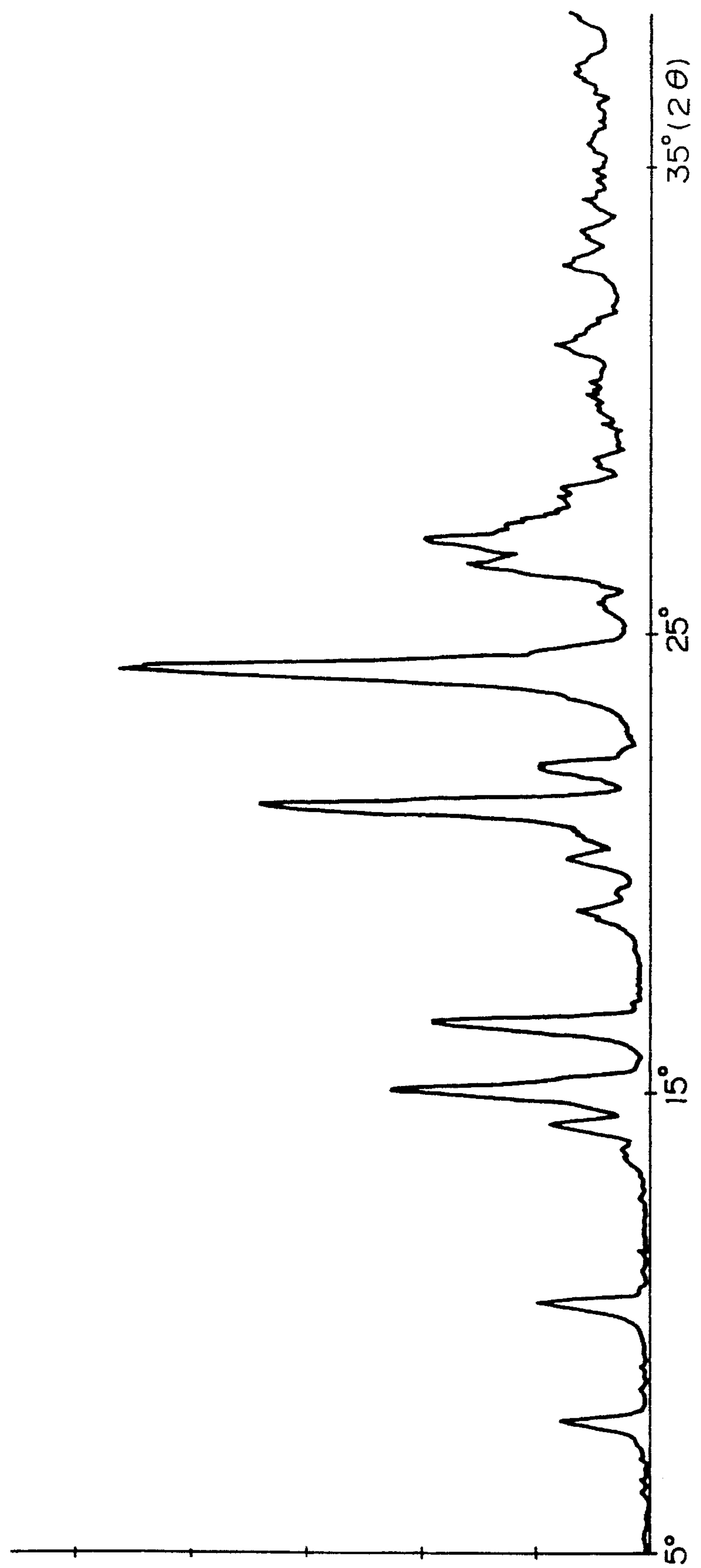
FIG. 11 is a powder X-ray diffraction spectrum for type I crystal of Q-35 in the initial state.
Figure 12:
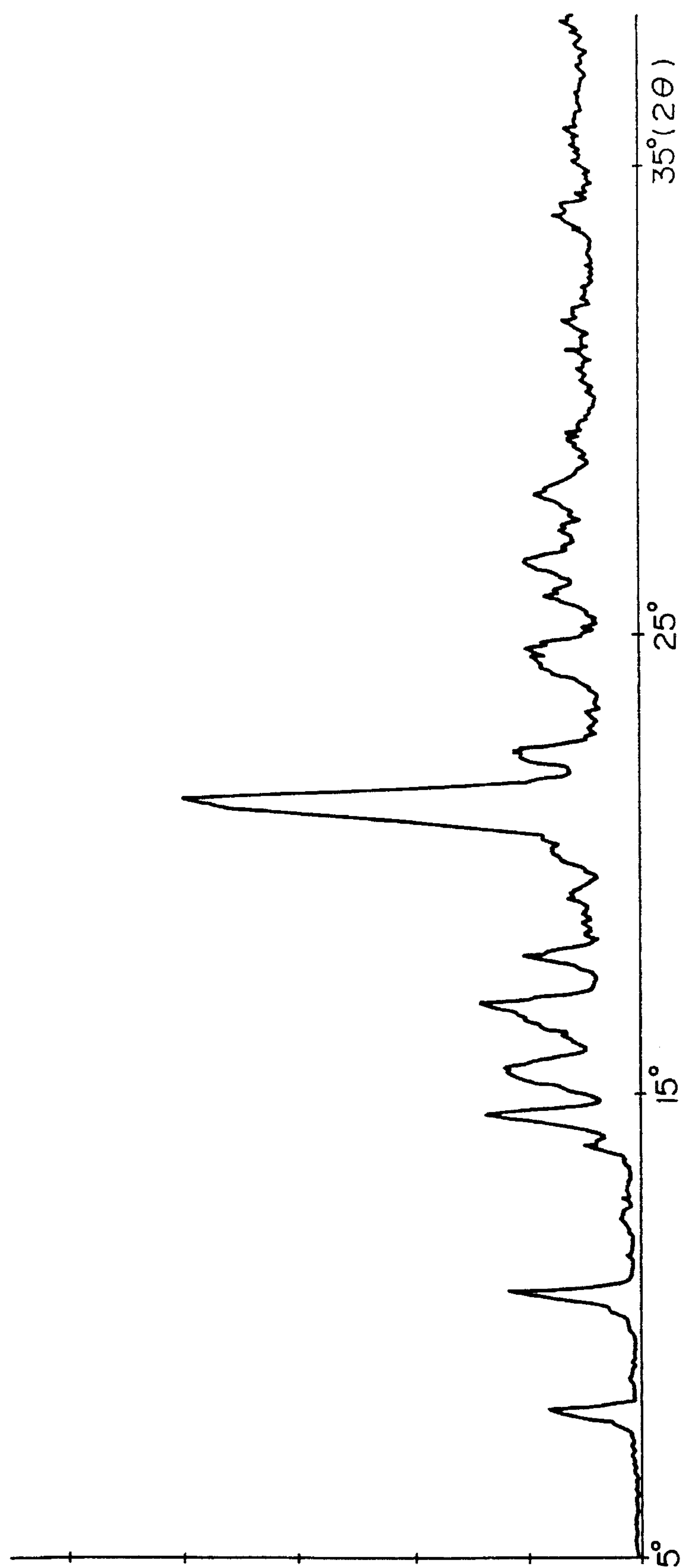
FIG. 12 is a powder X-ray diffraction spectrum for type I crystal of Q-35 in the heated state.
Figure 13:
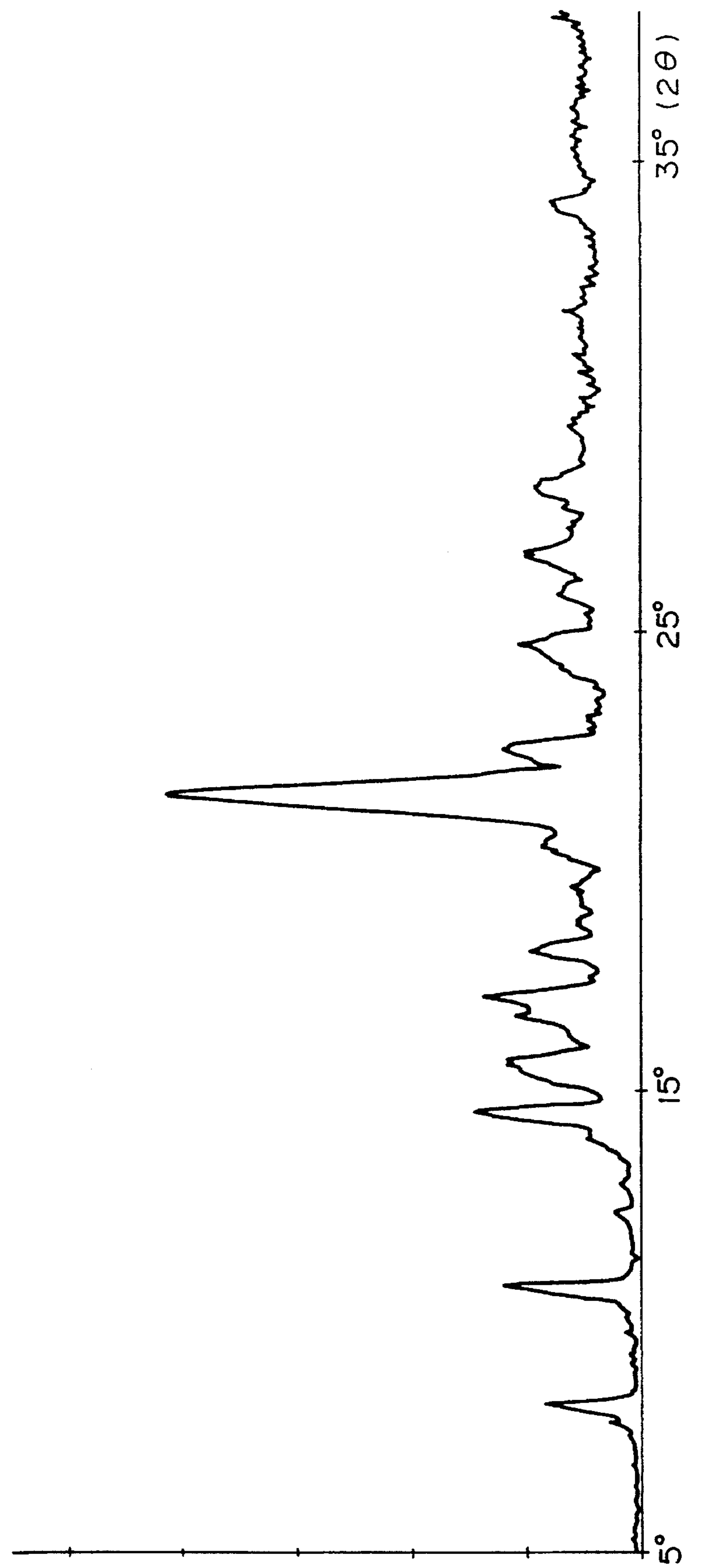
FIG. 13 is a powder X-ray diffraction spectrum for type I crystal of Q-35 as obtained when it was heated followed by cooling under dried conditions at storage at room temperature.
Figure 14:
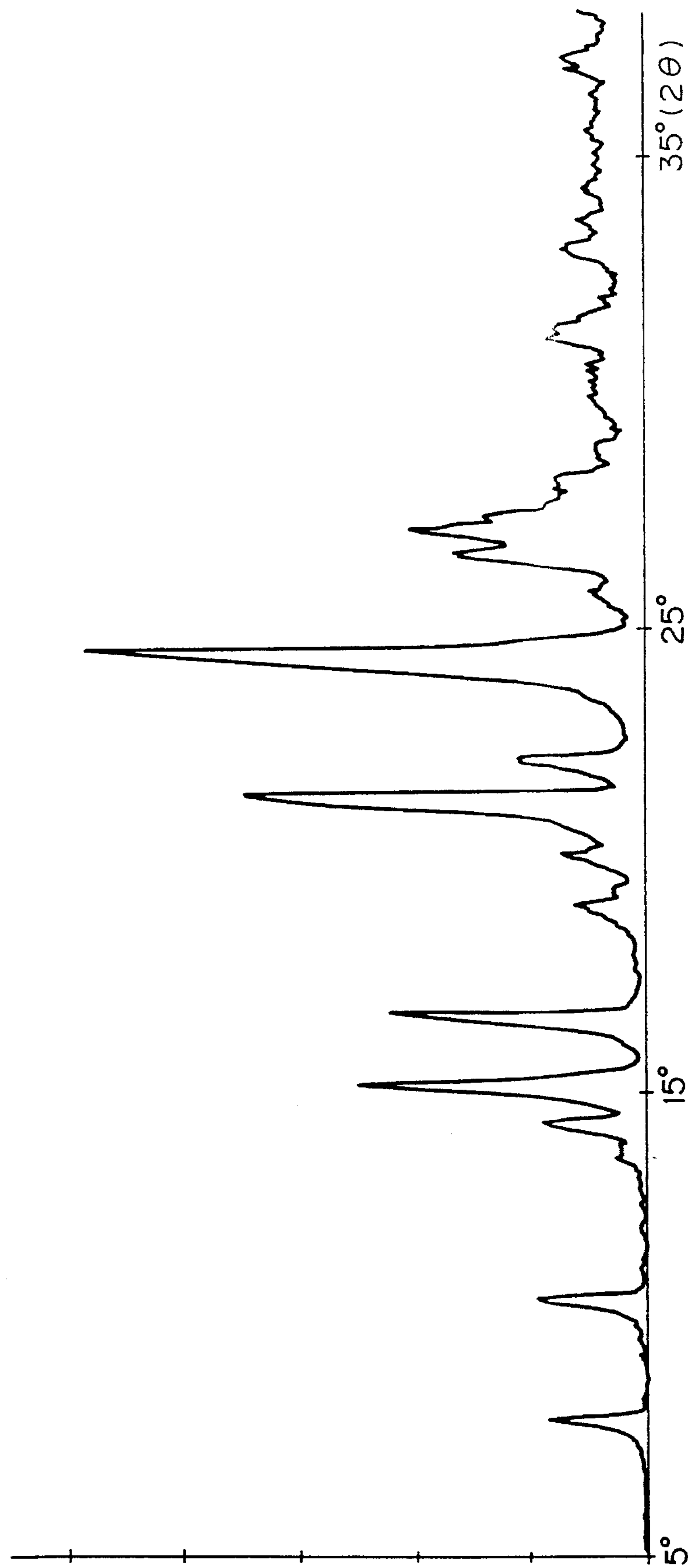
FIG. 14 is a powder X-ray diffraction spectrum for type I crystal of Q-35 as obtained when it was heated followed by cooling under dried conditions and storage under atmospheric conditions.

The spectrum for the initial state is shown in FIG. 11. Upon heating (80° C.), the large peak that occurred at 24.2° in the initial state disappeared and other aspects of the spectrum varied to produce an entirely different spectrum (FIG. 12). This result, taken in combination with the verification by an infrared absorption spectrum that dehydration was caused by heating, means that when dehydration occurred upon heating, not only was the molecule of water eliminated but also the crystal itself took on a different structure. When the crystal was subsequently cooled to room temperature under dried conditions, examination by an infrared absorption spectrum showed that the crystal retained the dehydrated state even when it was first cooled under dried conditions, then stored at room temperature. Powder X-ray diffraction also yielded a spectrum in agreement with the one obtained by heating (dehydration) showing the retention of the crystal structure of the dehydrated product (FIG. 13), with the crystal structure being the same as that of the dehydrated product obtained by heating. However, upon storage under atmospheric conditions, the large peak that occurred at 24.2° in the initial state appeared again in 14 h, yielding a spectrum in complete agreement with the initial spectrum (FIG. 14). It was already verified by an infrared absorption spectrum that upon storage under atmospheric conditions, water returned to have the crystal revert to the initial molecular structure. Now it was verified by powder X-ray diffraction, too, that upon storage under atmospheric conditions, the crystal structure of the dehydrated product reverted to the initial state, namely, the structure having two molecules of the water of crystallization. Combining the results of infrared absorption spectroscopy with those of powder X-ray diffraction, one can see that heating caused dehydration which, in turn, caused changes in the crystal structure but that upon storage under atmospheric conditions, water returned while, at the same time, the crystal structure also reverted to the initial state. Desorption of water was reversible and the hydrate and the dehydrate had different crystal structures and desorption of water was accompanied by a simultaneous change in the crystal structure, which change in the crystal structure was also reversible.

ii) Exposure to an Anhydrous Atmosphere at Room Temperature, Followed by Standing Under Atmospheric Conditions Infrared absorption spectroscopy revealed dehydration even upon exposure to an anhydrous atmosphere at room temperature and the change exhibited a similar behavior to the one that accompanied heating. Hence, examination was made in order to check whether a similar behavior would be exhibited in powder X-ray diffraction.

Figure 15:
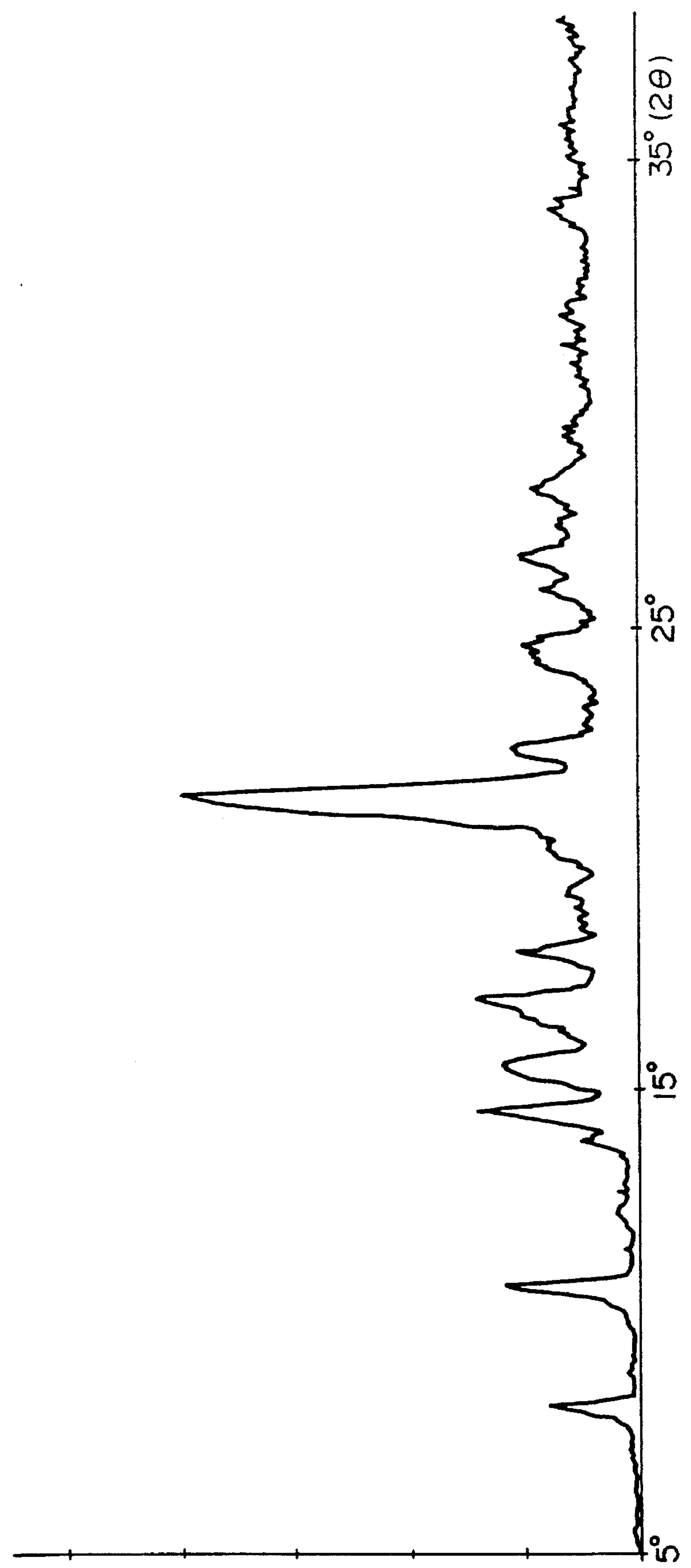
FIG. 15 is a powder X-ray diffraction spectrum for type I crystal of Q-35 in the heated state.
Figure 16:
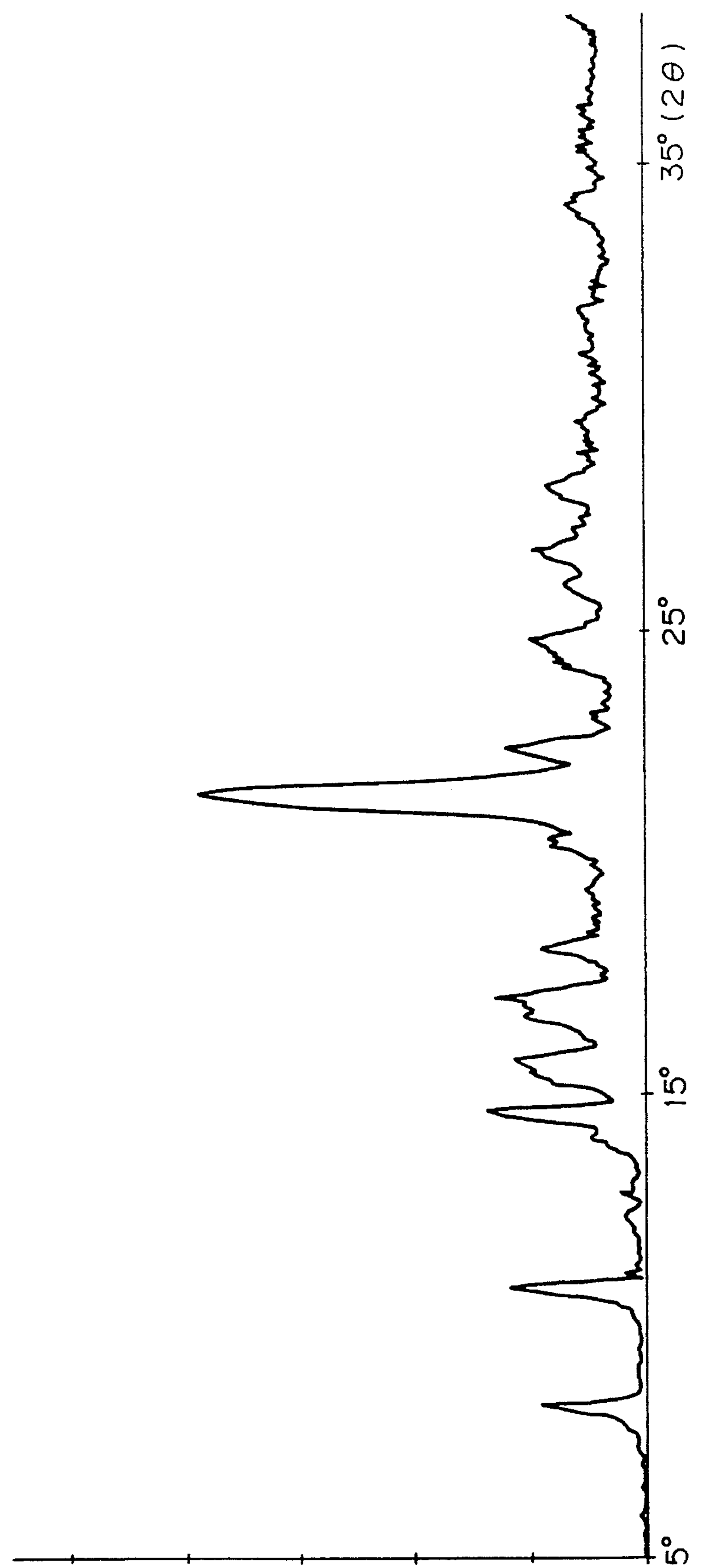
FIG. 16 is a powder X-ray diffraction spectrum for type I crystal of Q-35 after storage under dried conditions at room temperature.
Figure 17:
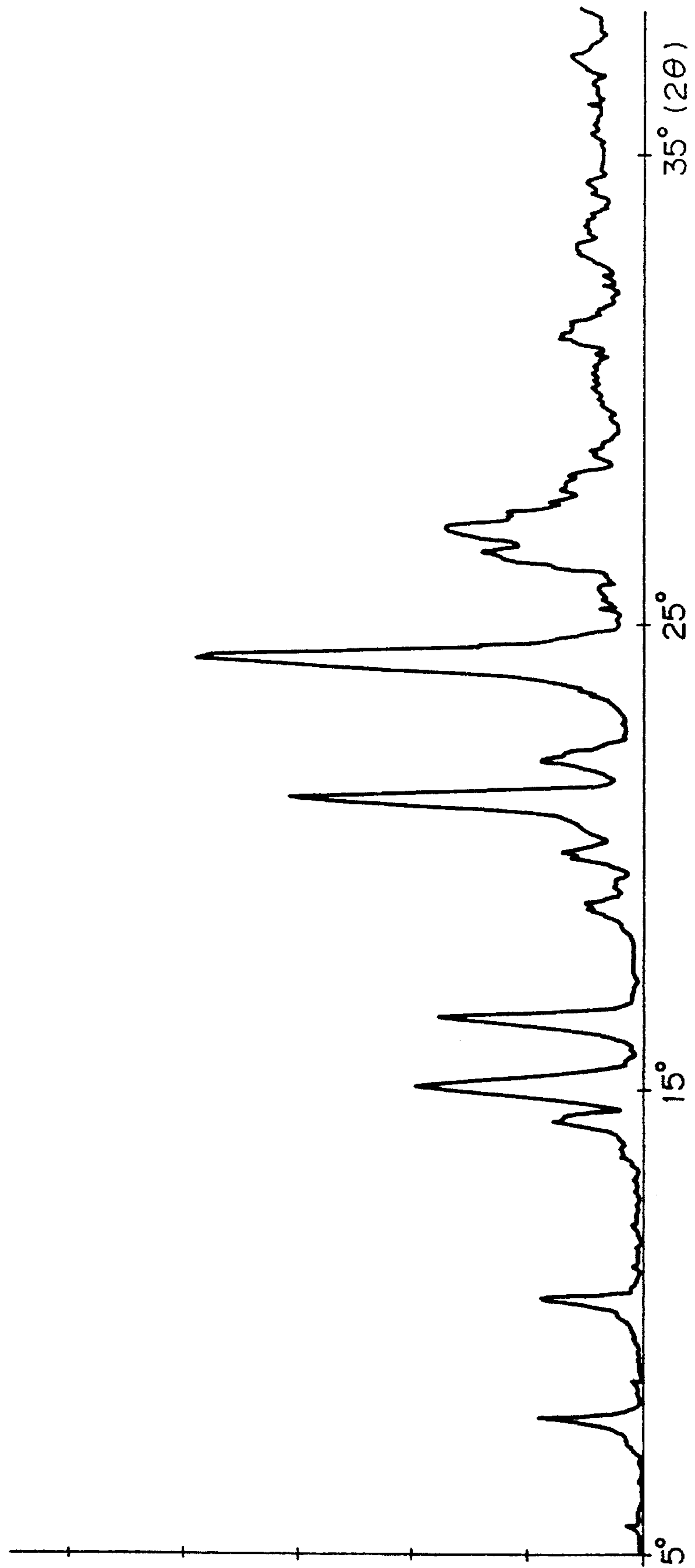
FIG. 17 is a powder X-ray diffraction spectrum for type I crystal of Q-35 as obtained when it was stored under dried conditions at room temperature, followed by storage under atmospheric conditions.
Figure 18:
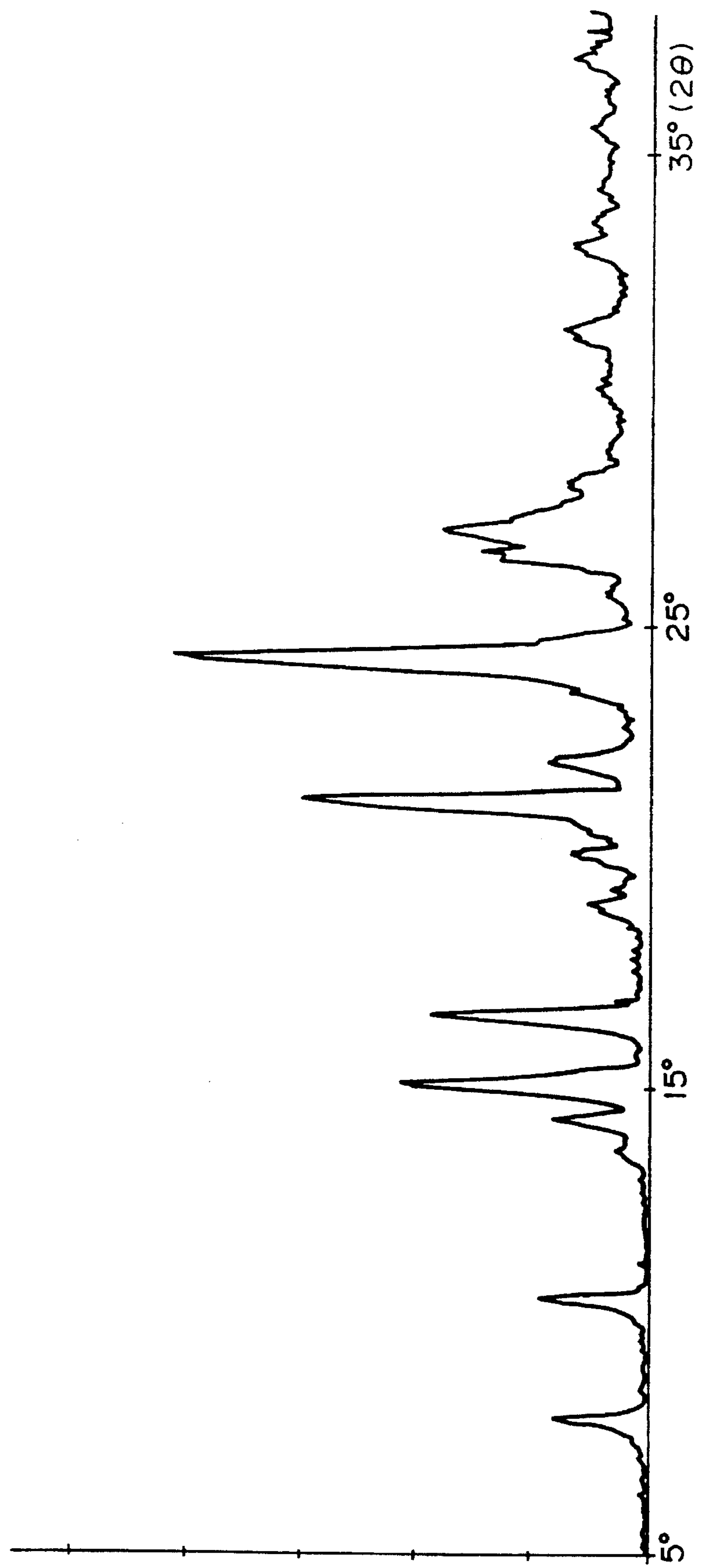
FIG. 18 is a powder X-ray diffraction spectrum for type I crystal of Q-35 in the initial state.

Upon storage under dried conditions, the spectrum changed over time until it agreed with the FIG. 15 spectrum after heating (dehydration) as shown in FIG. 16. Since it was already verified by an infrared absorption spectrum that dehydration occurred upon exposure to an anhydrous atmosphere at room temperature, the sample that had been stored under dried conditions for powder X-ray diffraction was a dehydrated product. The dehydrate after storage under dried conditions showed the same molecular structure in infrared absorption spectrum whether it had been heated or stored under dried conditions at room temperature. Similarly, said dehydrate was verified to have the same crystal structure as the dehydrate formed by heating. Upon storage under atmospheric conditions, the crystal produced a spectrum in 2 h that agreed completely with the FIG. 18 powder X-ray diffraction spectrum (as shown in FIG. 17). Infrared absorption spectroscopy showed that water returned to the crystal when it was stored under atmospheric conditions and powder X-ray diffraction also verified that as in the case of the changes due to heating, the sample reverted to the initial crystal structure of dihydrate.

These results showed the following: type I crystal of Q-35 dehydrated to become an anhydride either by heating or upon storage under dried conditions at room temperature and since the two dehydrated products assumed the same molecular and crystal structures, they were identical substances; when the dehydrates were stored under atmospheric conditions, they reverted to identical substances that took on the same molecular and crystal structures of dihydrate as in the initial state.

(3) Single-crystal X-ray Analysis

Infrared absorption spectroscopy and powder X-ray diffraction revealed that dehydration occurred under both heating and exposure to an anhydrous atmosphere at room temperature, with the dehydrated products assuming identical molecular and crystal structures; it was also found that upon storage under atmospheric conditions, the dehydrates reverted to the same molecular and crystal structures of dihydrate as in the initial state. To further support these facts, the inventors conducted single-crystal X-ray analyses.

Figure 19:
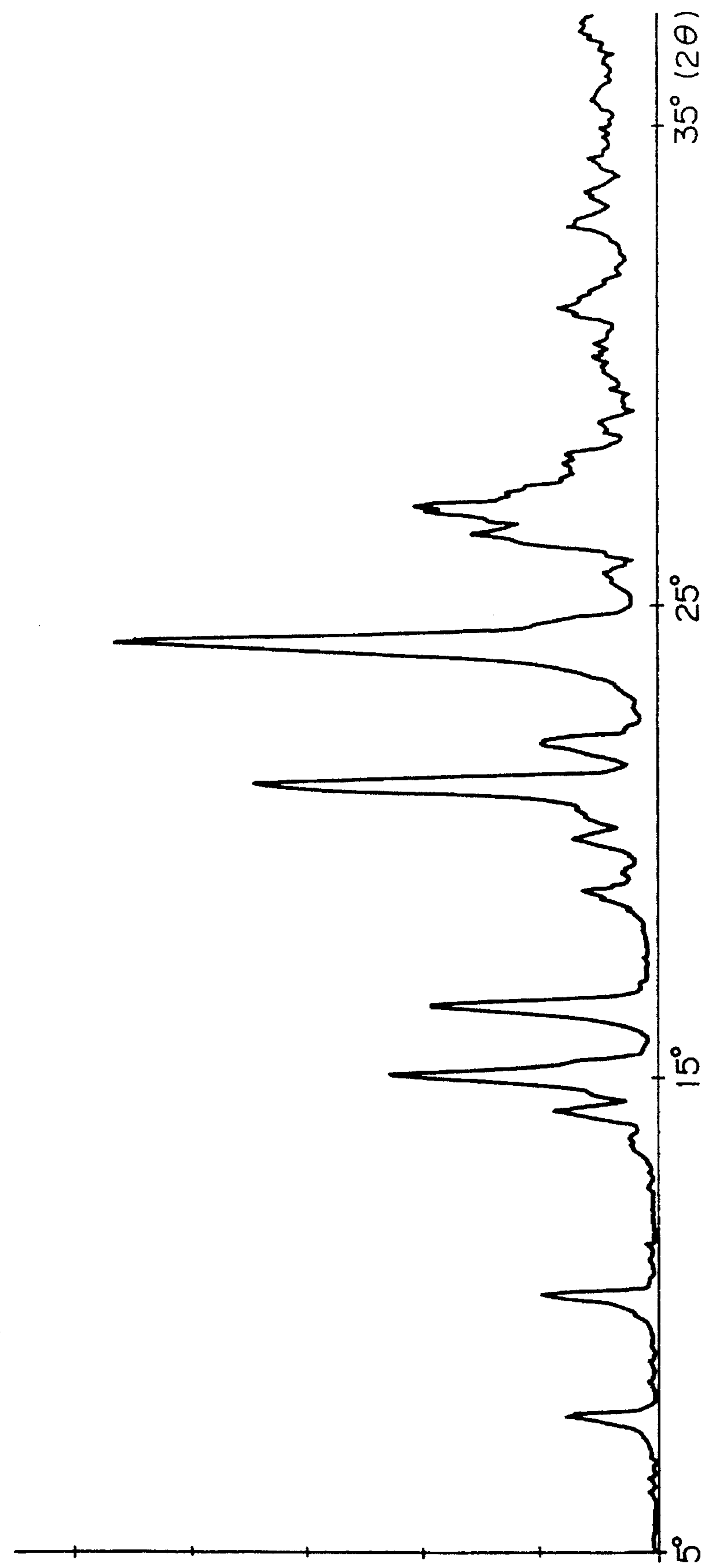
FIG. 19 is a powder X-ray diffraction spectrum for type I crystal of Q-35 in the initial state as it was placed under atmospheric conditions.
Figure 20:
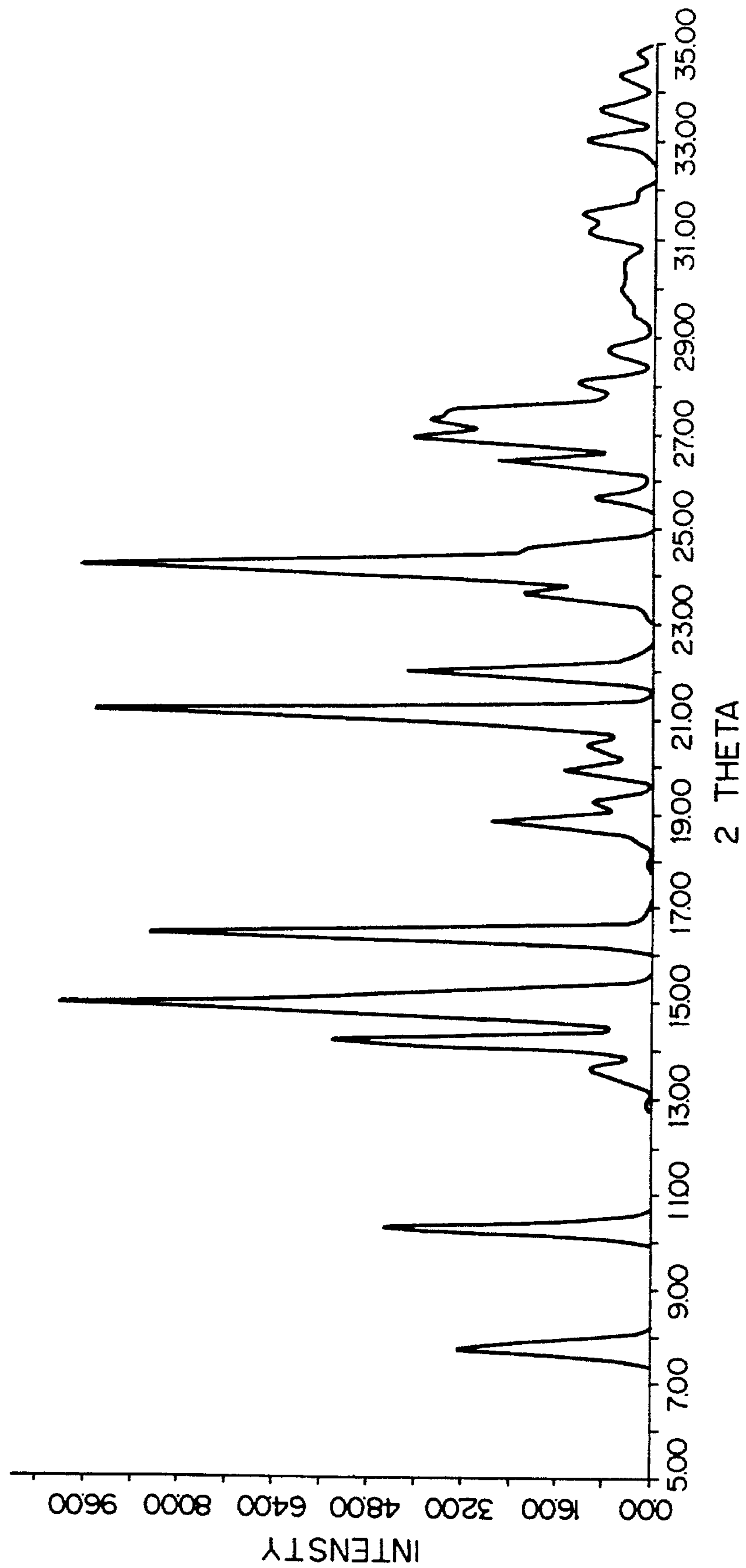
FIG. 20 is a composite spectrum for the powder X-ray diffraction of type I crystal of Q-35 in the initial state as obtained from the result of single-crystal X-ray analysis.
Figure 21:
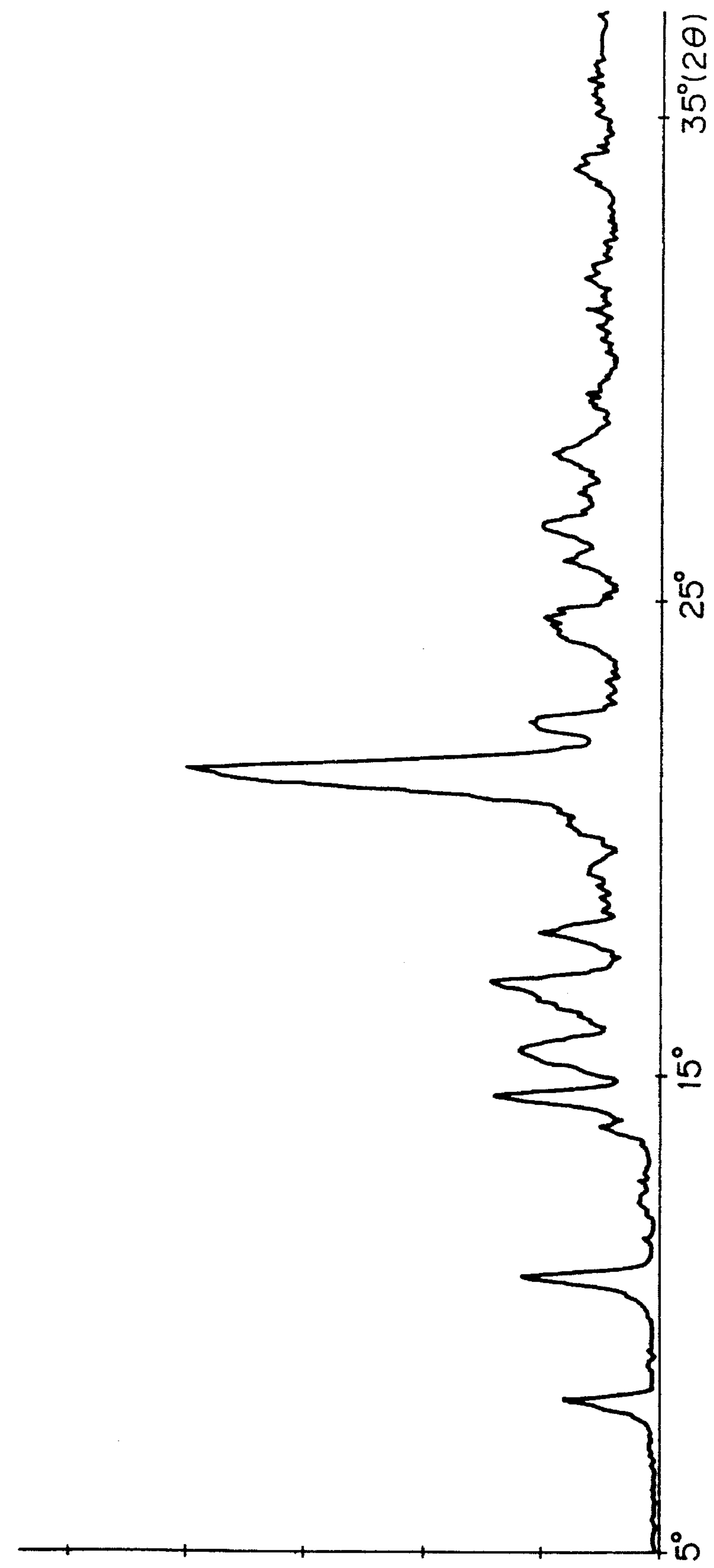
FIG. 21 is a powder X-ray diffraction spectrum for type I crystal of Q-35 in the heated state.
Figure 22:
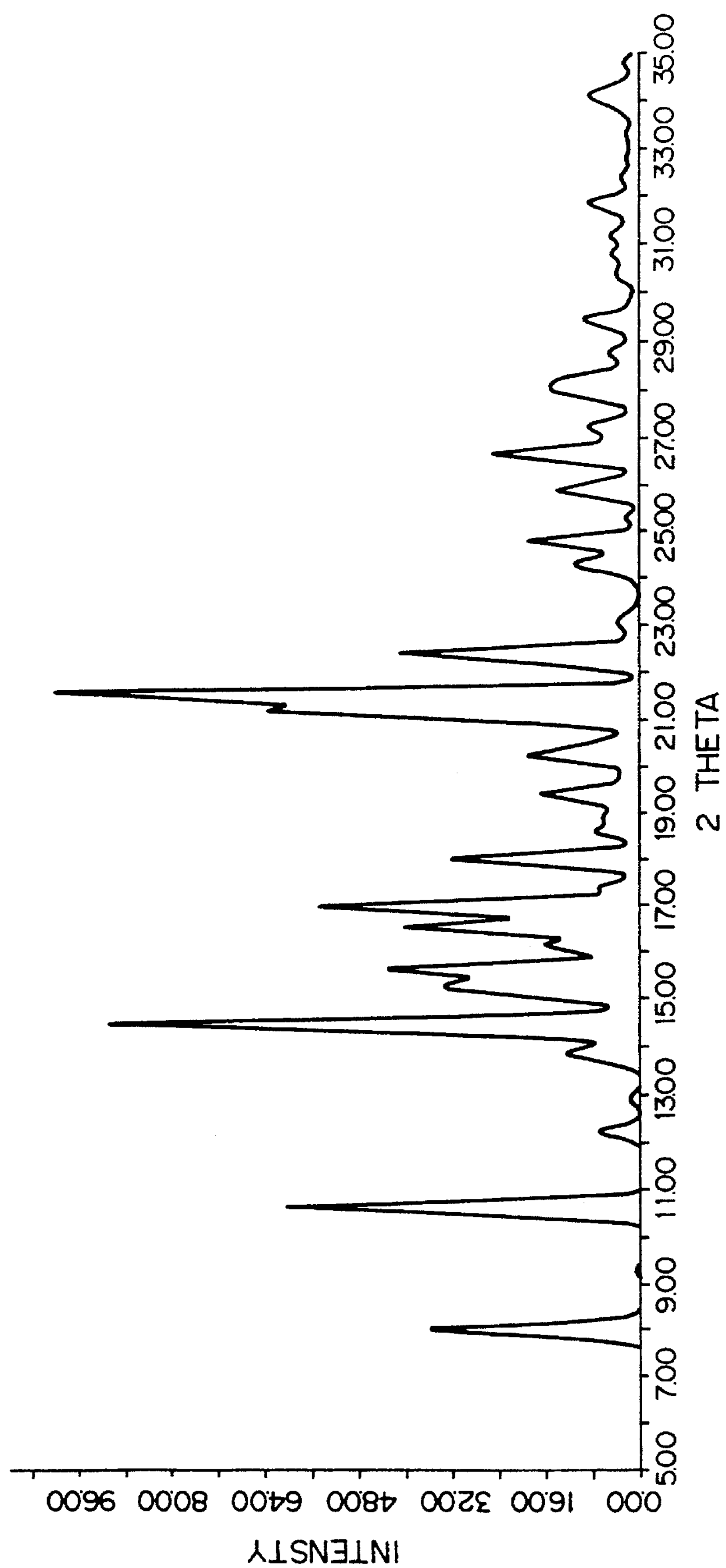
FIG. 22 is a composite spectrum for the powder X-ray diffraction of type I crystal of Q-35 under dried conditions at room temperature as obtained from the result of single-crystal X-ray analysis.

Samples of type I crystal of Q-35 were prepared for use in single-crystal X-ray analysis. On the basis of measurements conducted on these samples, a composite spectrum for powder X-ray diffraction was constructed and this was found to agree with the powder X-ray diffraction spectrum (FIG. 19) obtained upon standing under atmospheric conditions (as shown in FIG. 20). Subsequently, samples of type I crystal of Q-35 were also prepared for use in single-crystal X-ray analysis by drying an anhydrous atmosphere at room temperature. On the basis of measurements conducted on those samples, a composite spectrum for powder X-ray diffraction was constructed and this was found to agree with the FIG. 21 X-ray diffraction spectrum obtained by heating and subsequent exposure to an anhydrous atmosphere at room temperature (as shown in FIG. 22). Hence, it was verified that the dried single crystal had been dehydrated.

The dehydrated single crystal had experienced a change in lattice constant (initial: b=12.966 (2) Å; dehydrated crystal: b=38.34 (2) Å; no change in a, c and β), with the resulting change in the structure of the trimer.

Figure 23:
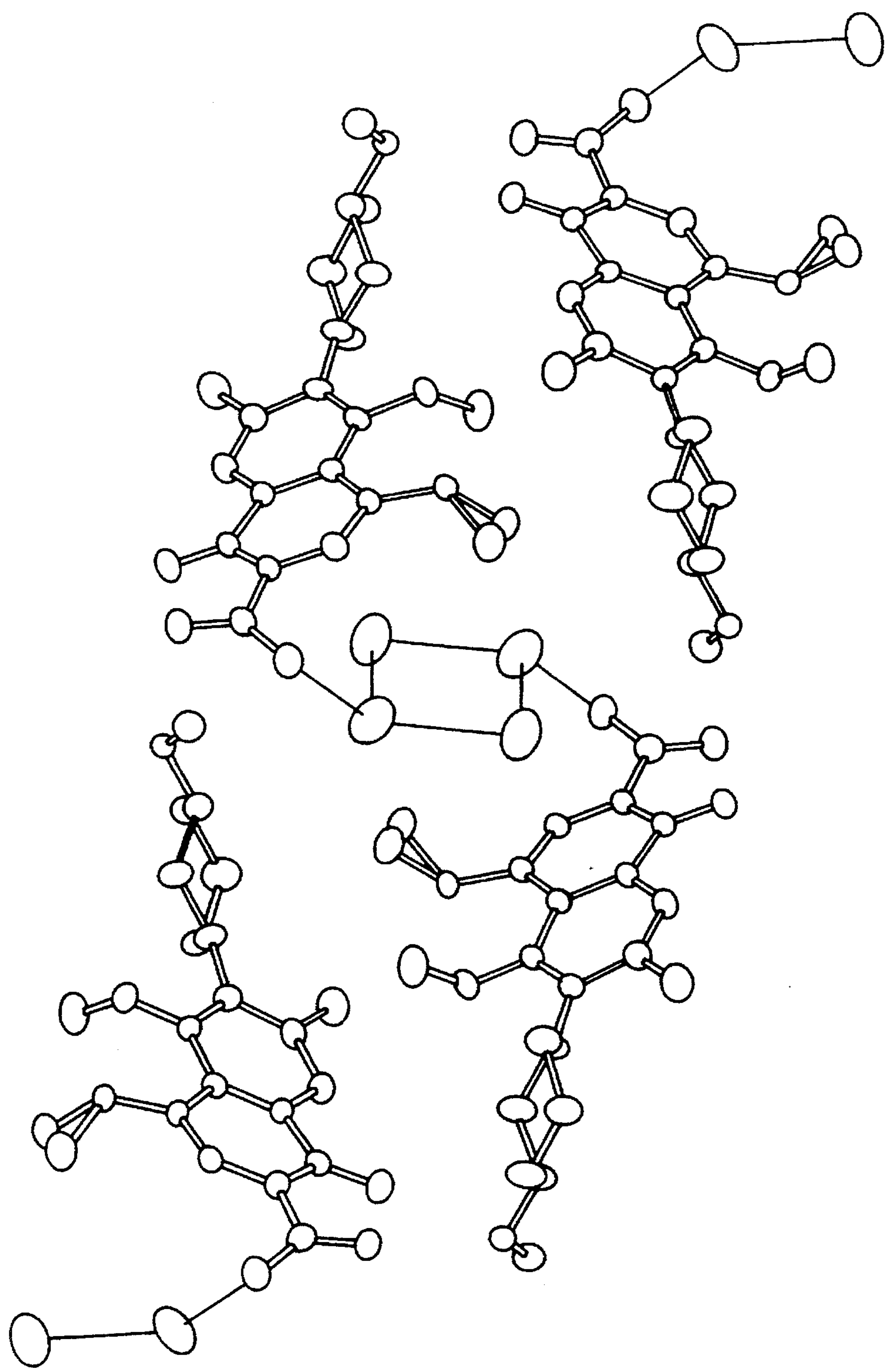
FIG. 23 shows the crystal structure of type I crystal of Q-35 in the initial state.
Figure 24:
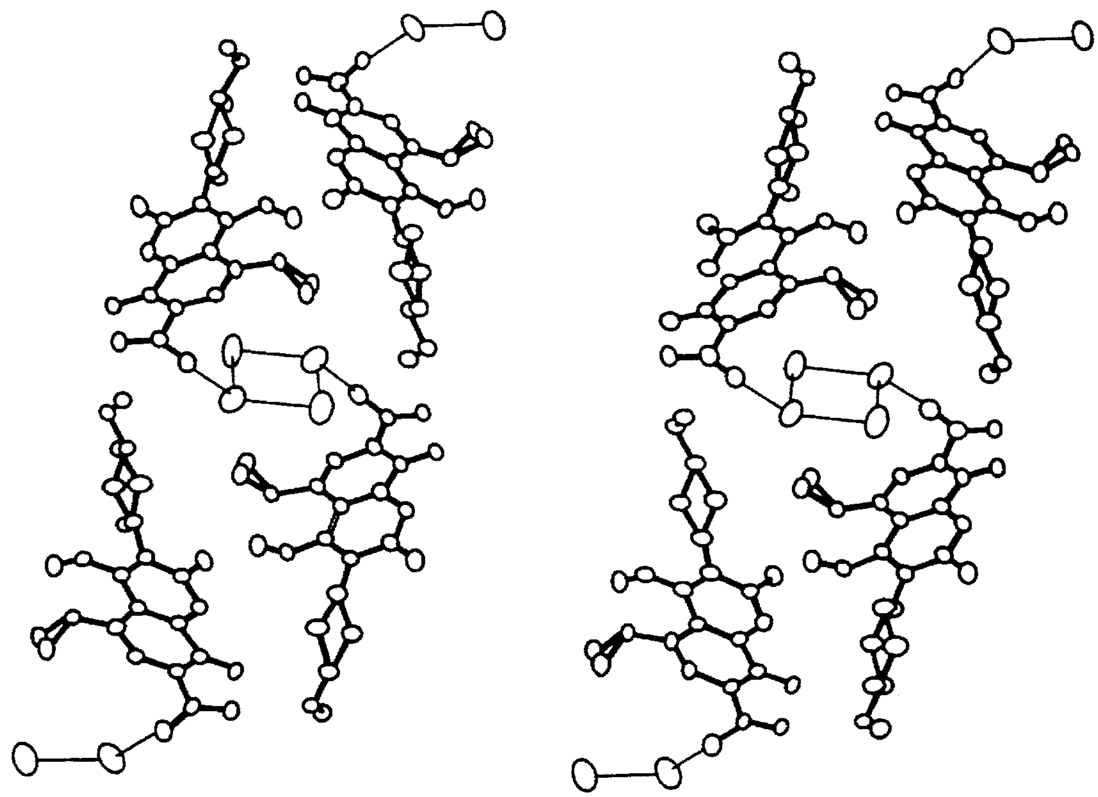
FIG. 24 shows stereographically the crystal structure of type I crystal of Q-35 in the initial state.
Figure 25:
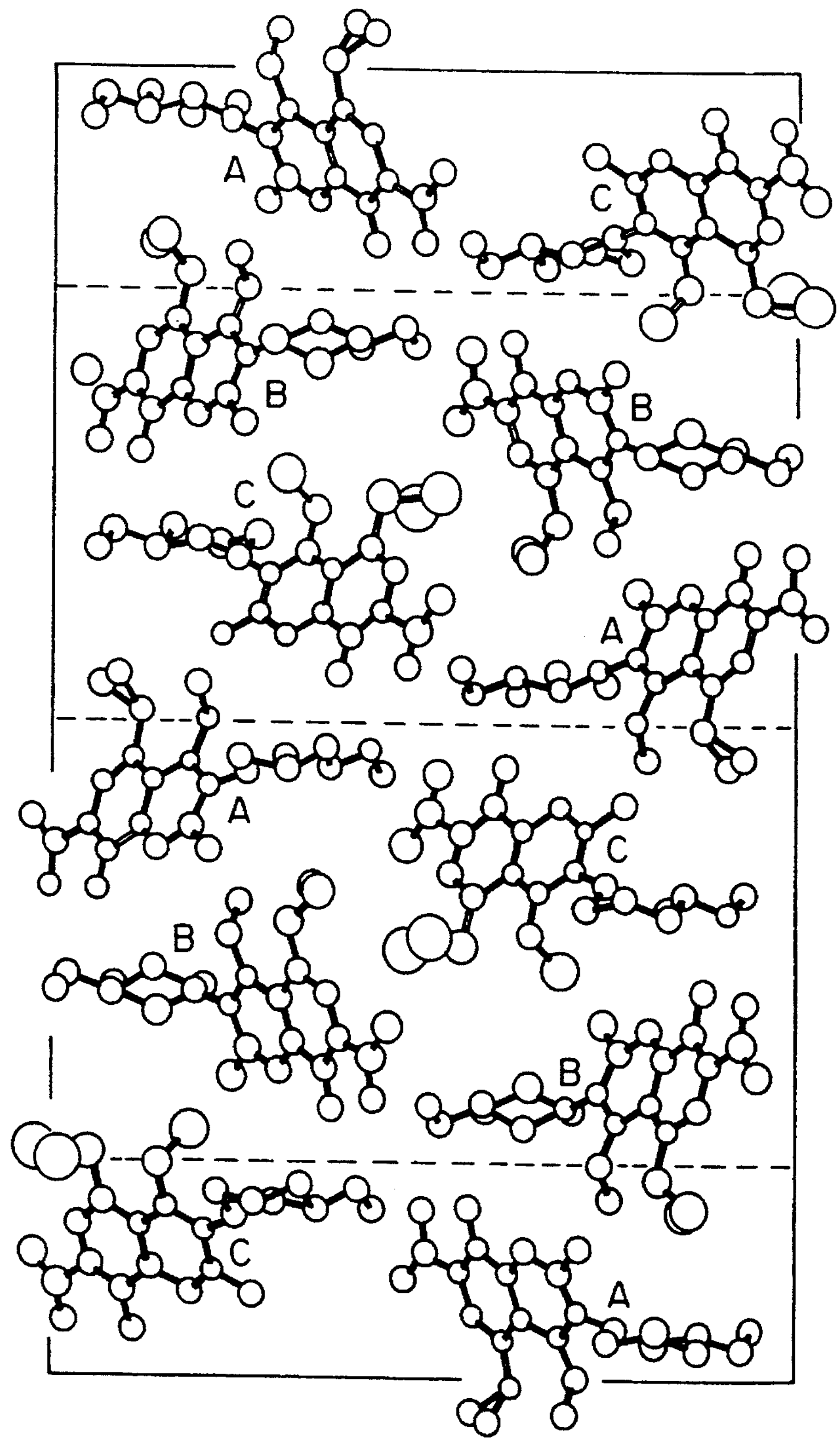
FIG. 25 shows the crystal structure of type I crystal of Q-35 under dried conditions at room temperature (as a dehydrated product)
Figure 26:
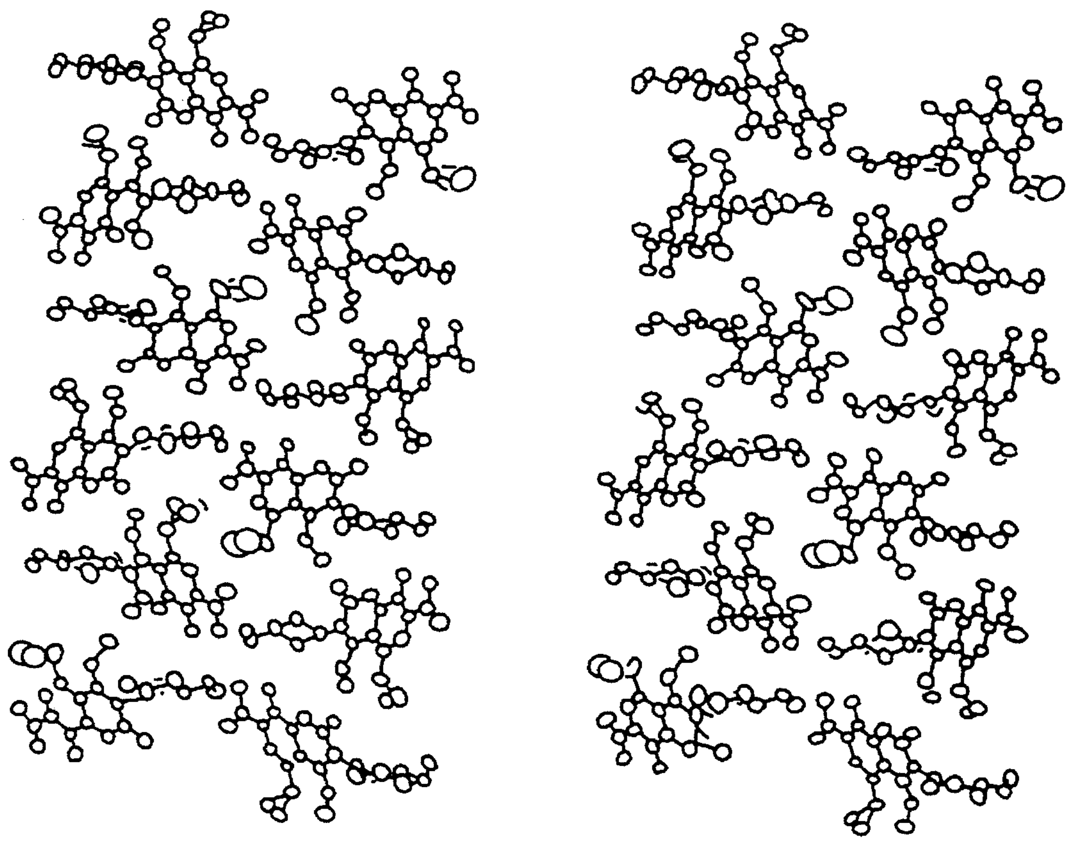
FIG. 26 shows stereographically the crystal structure of type I crystal of Q-35 under dried conditions at room temperature (as a dehydrated product)
Figure 27:
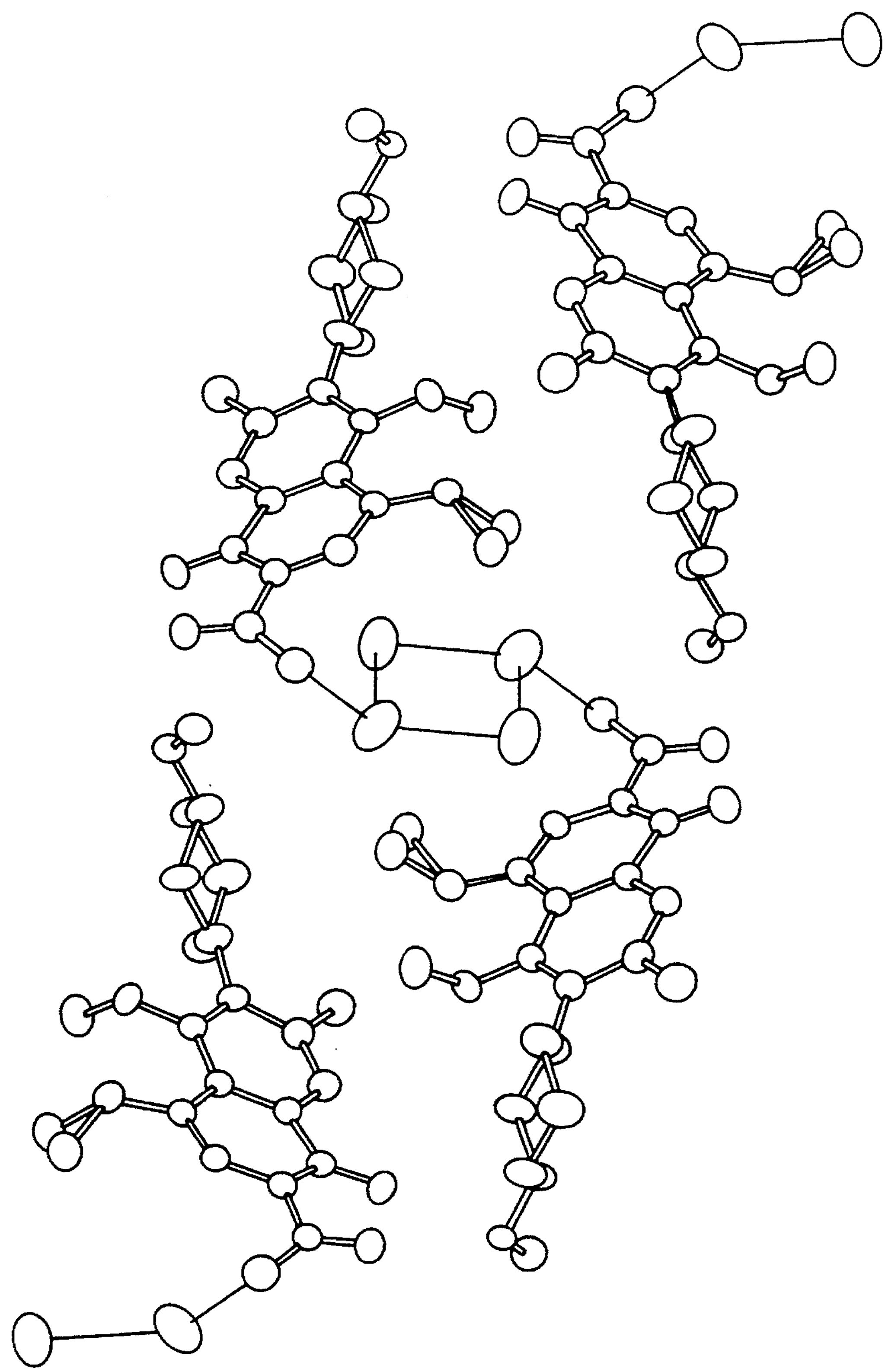
FIG. 27 shows the crystal structure of type I crystal of Q-35 as stored under dried conditions at room temperature, followed by storage under atmospheric conditions.
Figure 28:
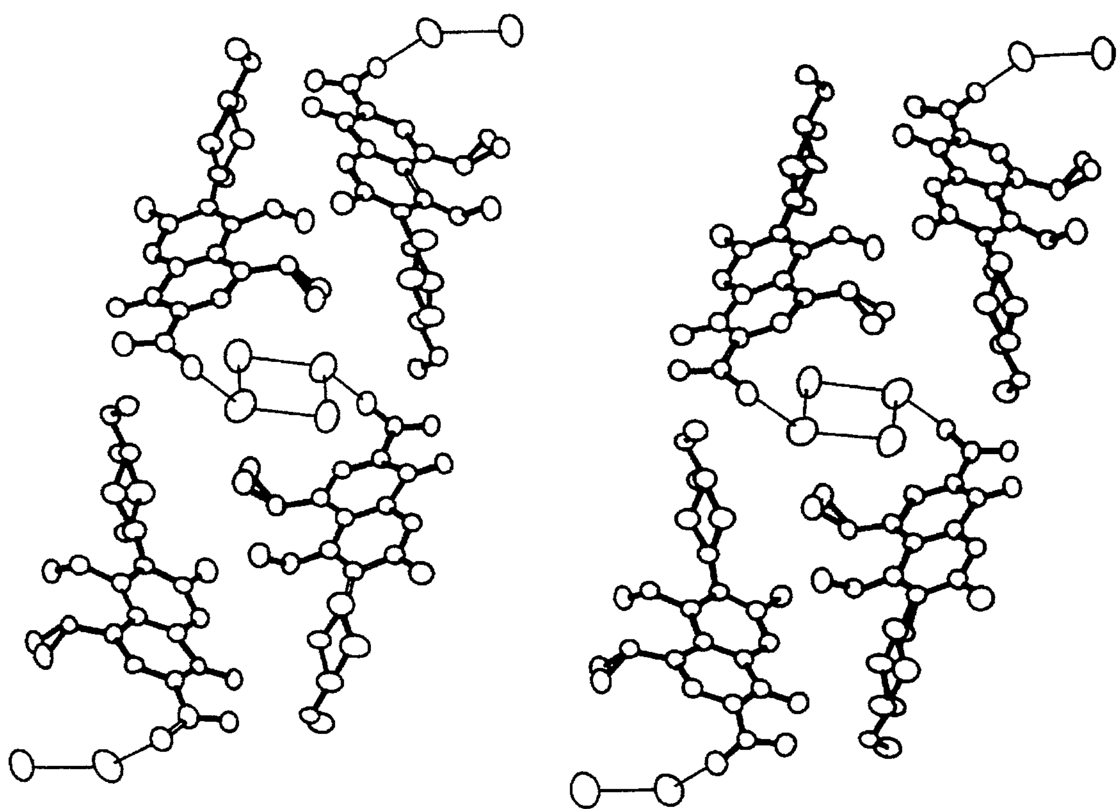
FIG. 28 shows stereographically the crystal structure of type I crystal of Q-35 as stored under dried conditions at room temperature, followed by storage under atmospheric conditions.

Crystal structural diagrams for the initial state are shown in FIGS. 23 and 24; crystal structural diagrams for the dehydrated product are shown in FIGS. 25 and 26. The crystal that had been dried under dried conditions at room temperature was stored under atmospheric conditions and subjected to measurements again; the sample was verified to have the same crystal structure as in the initial state (FIGS. 27 and 28).

Powder X-ray diffraction showed that the hydrate and the dehydrate had different crystal structures and the structural change involved was reversible; these results were also supported by single-crystal X-ray analysis.

5) Conclusion

The foregoing experimental results made the following points clear about the behavior of the water of crystallization in type I crystal of Q-35.

By heating or storage under dried conditions at room temperature, dehydration as accompanied by changes in the crystal structure occurred to produce anhydrides.

Irrespective of the drying conditions employed as to whether it was by heating or by storage under dried conditions at room temperature, the dehydrated products had the same molecular and crystal structures.

The amount of dehydration agreed quantitatively with the theoretical value of water content in the dehydrate.

Upon storage under atmospheric conditions, the dehydrate absorbed moisture in air to revert to type I crystal of Q-35.

Desorption of water was reversible.

The amount of water absorption by the dehydrates agreed quantitatively with the theoretical value for two molecules of water.

The dehydrates changed to type I crystal of Q-35 in the presence of the slightest amount of water in the atmosphere it is placed; hence, the water of crystallization in type I crystal of Q-35 is stable as long as it is handled in the usual manner.

As already mentioned herein, type III crystal of Q-35 has very poor stability. In contrast, type I crystal (dihydrate) and type II (monohydrate) of Q-35, both of which dehydrate under drying conditions to become anhydrides, have been verified to absorb moisture in air again upon storage under atmospheric conditions to revert to the initial type I and type II crystals, respectively, of Q-35. Under the circumstances, tests were conducted to compare the stability of the two types of crystal by the methods described below, giving the results also described below.

Test 1—Moisture Absorption Test

Type I crystal and type II crystal of Q-35 were each placed at 40° C. and left to stand under varying humidity conditions of 0% R.H., 52.4% R.H., 75% R.H. and 100% R.H. to investigate the weight changes that occurred 4–7 days later. The results are shown in Table 1.

TABLE 1

| | Weight changes at 40° C. and at varying humidified conditions | | | | |
|---|---|---|---|---|---|
| | Sample | Days (%) | | | |
| | (mg) | 4 | 5 | 6 | 7 |
| (Type II crystal) | | | | | |
| 0% R.H. | 113.0 | −2.57 | −2.48 | −2.12 | −2.48 |
| 52.4% R.H. | 129.1 | 0.31 | −0.15 | −0.08 | −0.15 |
| 75% R.H. | 113.0 | 0.53 | 0.53 | 0.62 | 0.62 |
| 100% R.H. | 118.9 | 3.78 | 4.46 | 4.46 | 4.71 |
| (Type I crystal) | | | | | |
| 0% R.H. | 127.9 | −4.53 | −8.29 | −8.21 | −8.05 |
| 52.4% R.H. | 132.5 | 0.38 | 0.23 | 0.30 | 0.53 |
| 75% R.H. | 192.5 | 0.42 | 0.47 | 0.26 | 0.42 |
| 100% R.H. | 129.1 | 0.70 | 0.39 | 0.39 | 0.34 |

Type II crystal experienced a little more than 2% weight loss at 0% R.H. but its weight change was no more than 1% at 52.4% R.H. and 75% R.H. However, its weight increased by about 5% at 100% R.H. On the other hand, type I crystal experienced about 8% weight loss at 0% R.H. but the change was within 1% at all other relative humidities. At lower humidities, type I crystal would lose the water of crystallization.

Figure 29A:
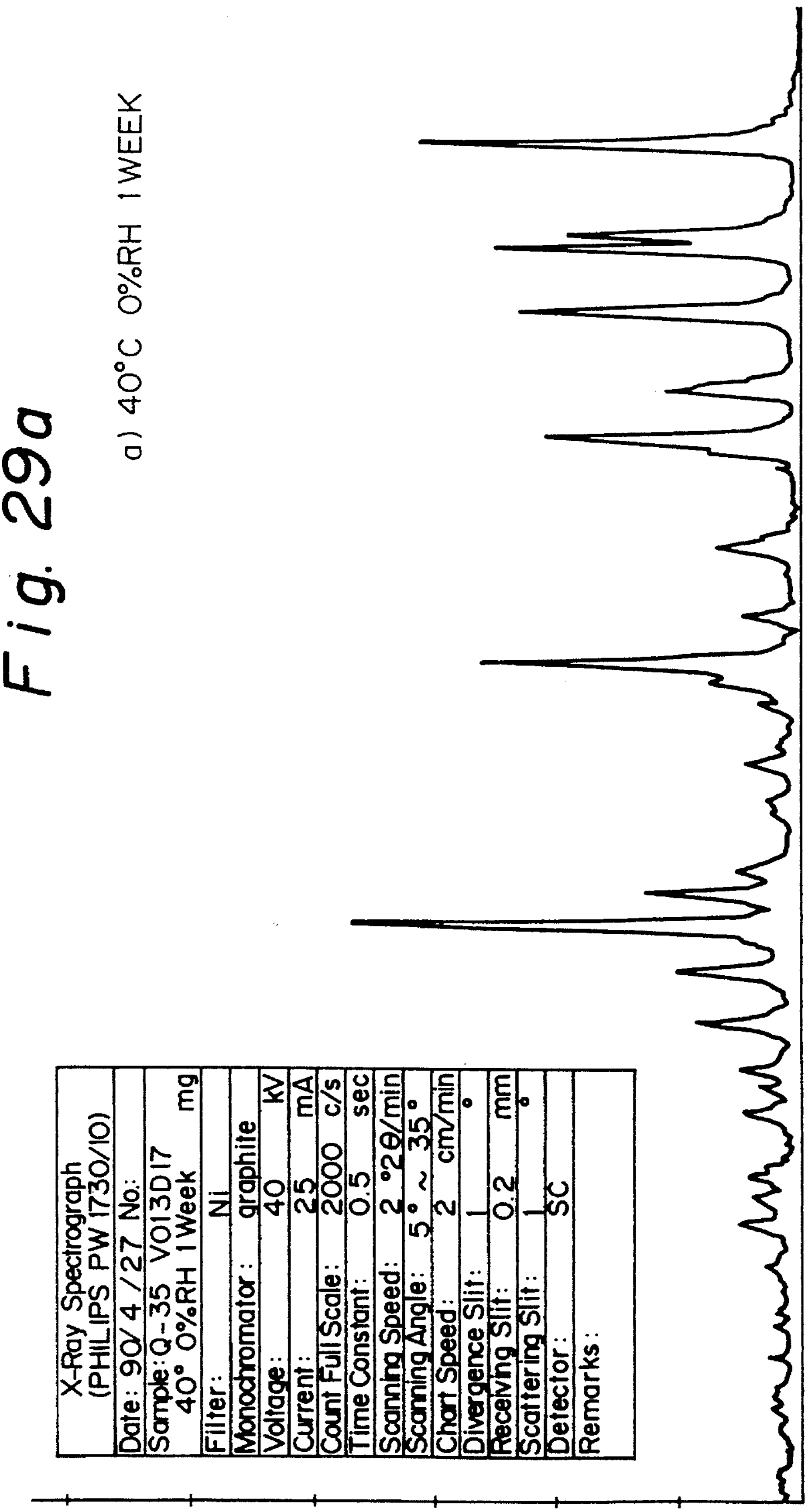
FIG. 29 shows powder X-ray diffraction spectra for type II crystal of Q-35 as stored in humidified conditions, FIG. 29*a* showing a powder X-ray diffraction spectrum for the case of storage at 40° C.×0% R.H. for one week, FIG. 29*b* for storage at 40° C.×75% R.H. for one week, and FIG. 29*c* for storage at 40° C.×100% R.H. for one week.
Figure 29B:
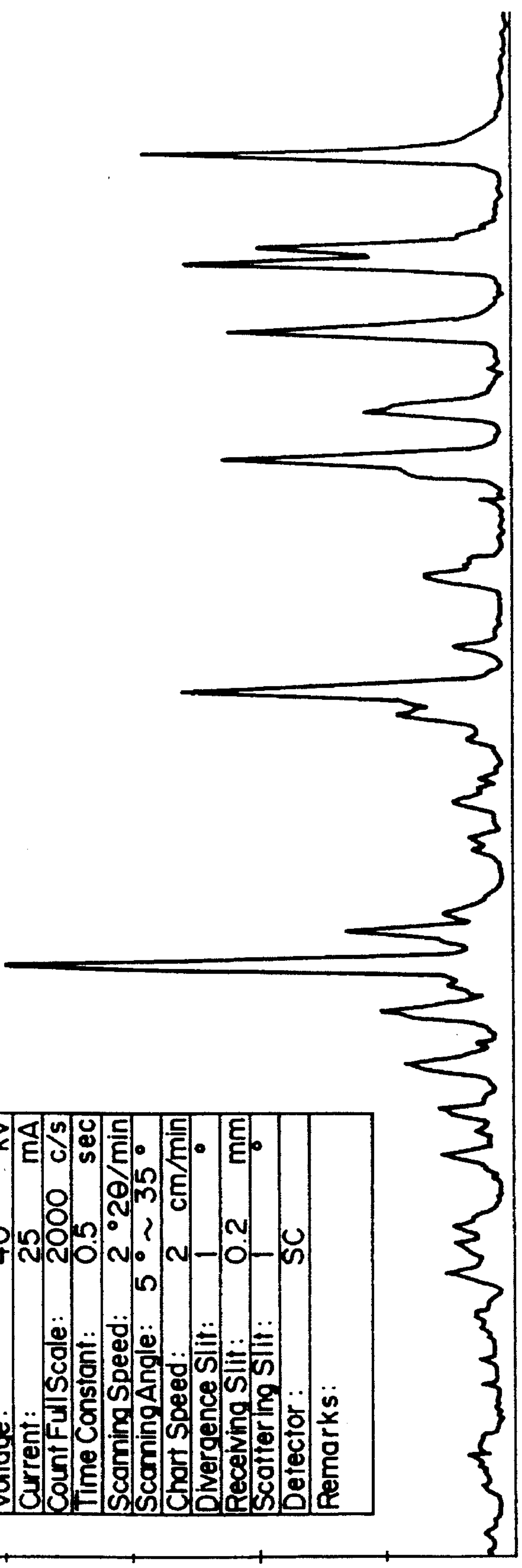
Figure 29C:
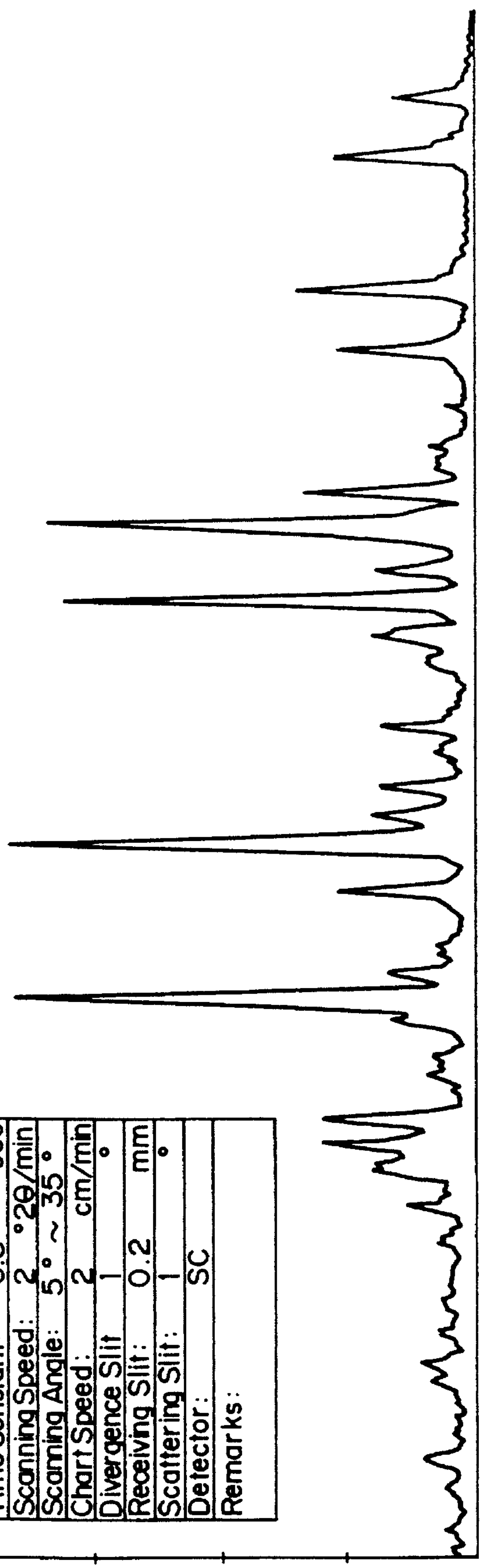

When type II crystal was stored at 40° C. for 1 week at 0% R.H. and 75% R.H., the resulting powder X-ray diffraction spectra (FIGS. **29*a* and 29*b*) both agreed with the initial spectrum for type II crystal; however, the spectrum (FIG. 29*c***) obtained after storage at 40° C. for 1 week at 100% R.H. did not agree with the initial spectrum for type II crystal and was estimated to be a mixture of spectra for diffraction peaks of type I and type III crystals.

Figure 30:
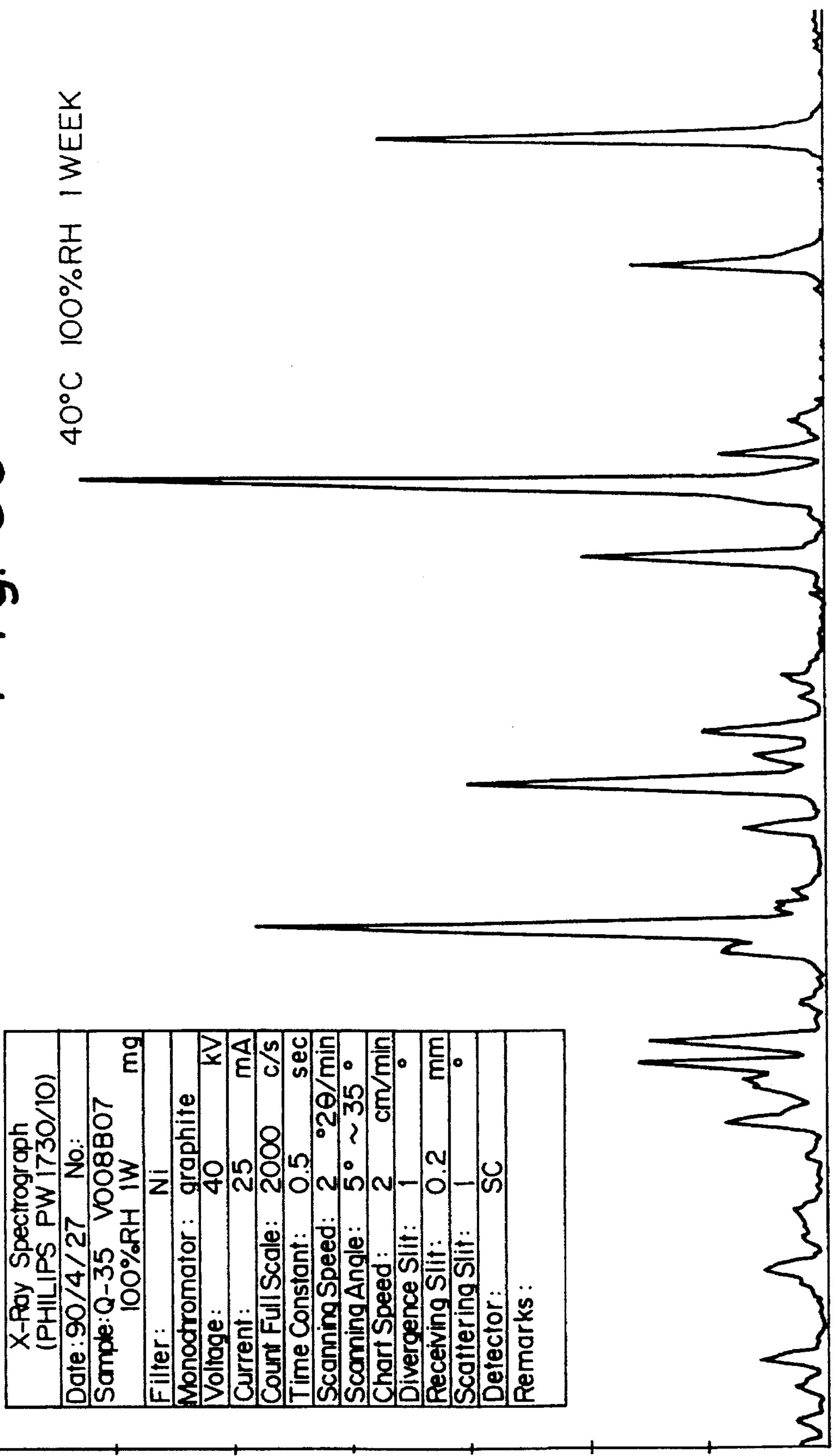
FIG. 30 is a powder X-ray diffraction spectrum for type I crystal of Q-35 as stored at 40° C.×100% R.H. for one week.

On the other hand, the powder X-ray diffraction spectrum (FIG. 30) for type I crystal that was stored at 40° C. for 1 week at 100% R.H. agreed with the initial spectrum for type I crystal.

From these results, one may well conclude that type I crystal is more advantageous than type II crystal in terms of pharmaceuticals manufacture for the reason that although it experiences a weight change at 0% R.H. (under drying conditions) on account of the loss of the water of crystallization, type I crystal, when placed at high humidities, does not exhibit any marked moisture absorption, nor does it involve any crystal dislocation.

Test 2—Effects of Blending

Q-35, when it is to be used as a medicine, is held to be suitably formulated as an oral preparation of 100–200 mg. Therefore, the formulation would have a high content of active ingredient, presenting a strong need for performing wet granulation. Hence, in simulated wet granulation, blending was done in water and/or ethanol to check whether the crystal form would change or not; to this end, each of type II and I crystals was blended in ethanol, 50% aqueous ethanol solution or water and, thereafter, powder X-ray diffraction spectra were measured.

Figure 31A:
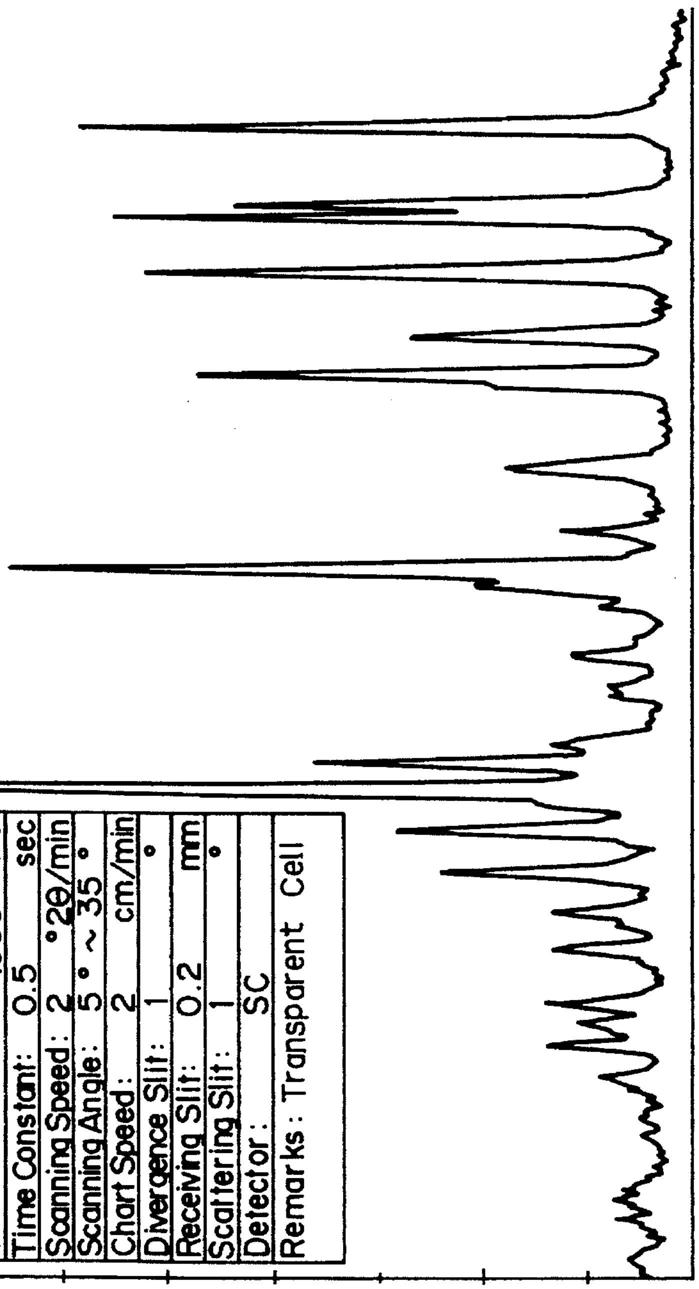
FIG. 31 shows powder X-ray diffraction spectra for type II crystal of Q-35 after blending, FIG. 31*a* showing a powder X-ray diffraction spectrum for a powder blended in ethanol, FIG. 31*b* for a powder blended in an aqueous solution of 50% ethanol, and FIG. 31*c* for a powder blended in water.
Figure 31B:
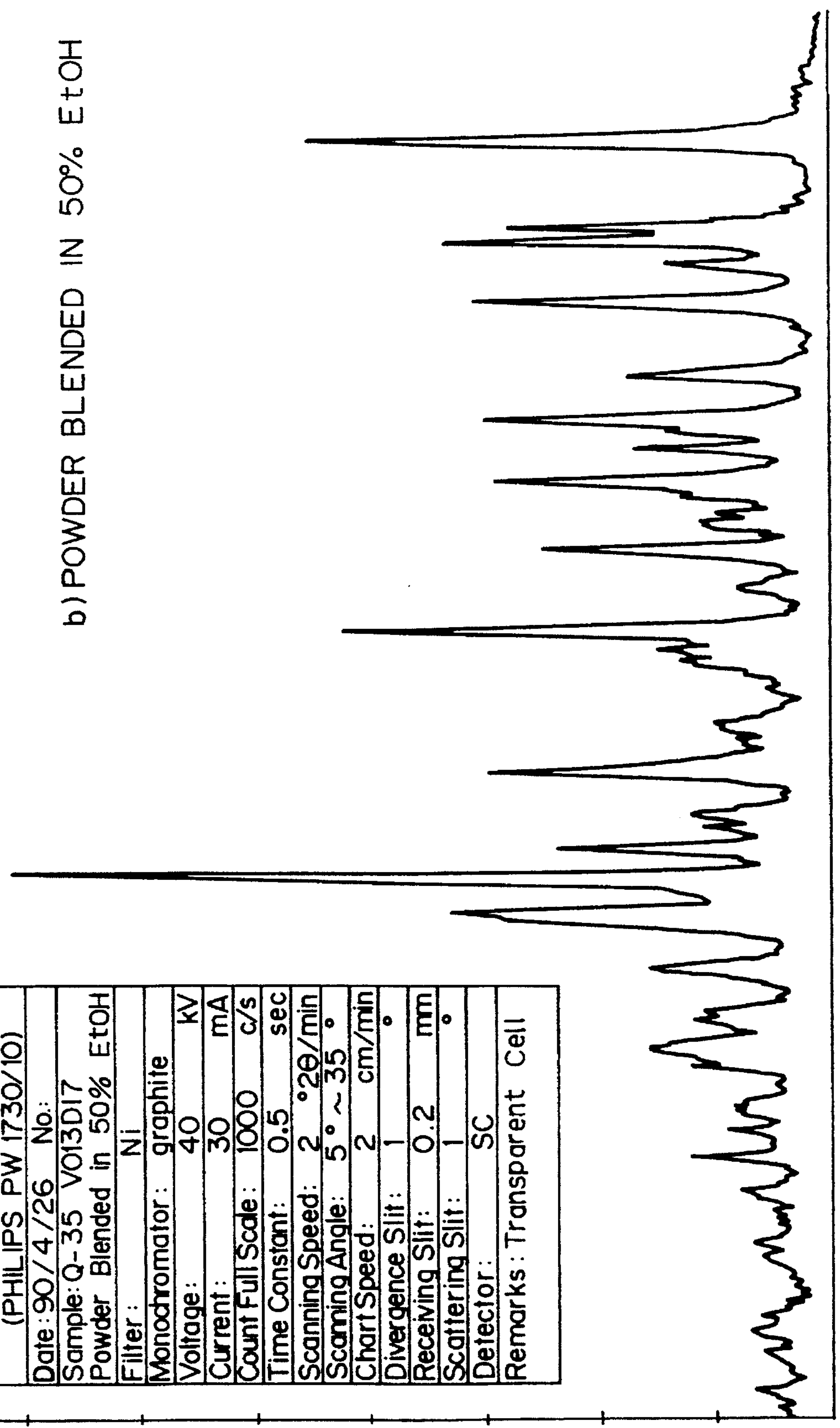
Figure 31C:
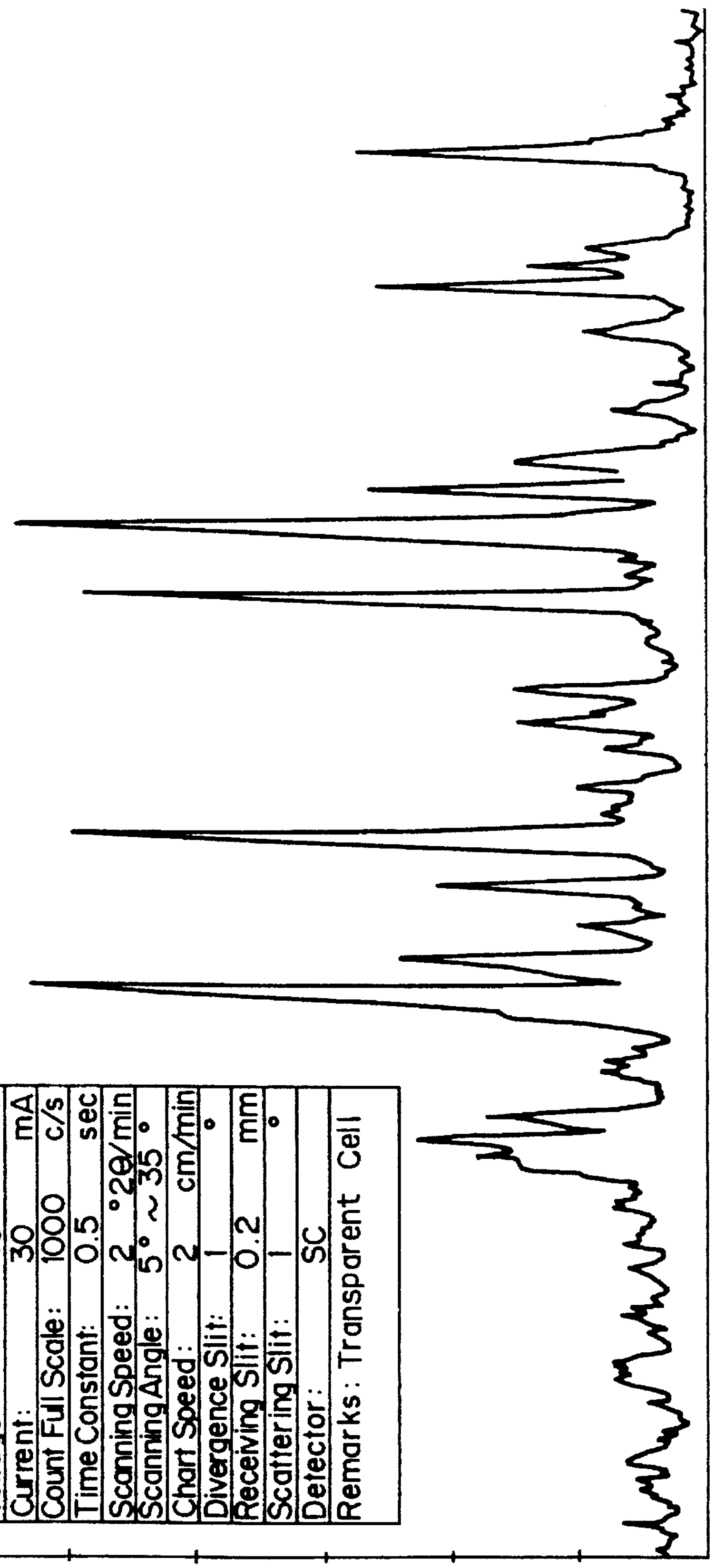

The powder of type II crystal, when blended in ethanol, provided a powder X-ray diffraction spectrum (FIG. **31*a***)

that agreed with the one for the initial type II crystal, thus showing that there was no change in the crystal form. However, when blended in 50% aqueous ethanol solution or water, the powder gave a mixture of diffraction peaks for type II crystal and type I crystal (FIGS. 31*b* and 31*c*). It was thus verified that type II crystal, when blended using a solvent with no more than 50% ethanol content, shifted partially to type I crystal.

Figure 32A:
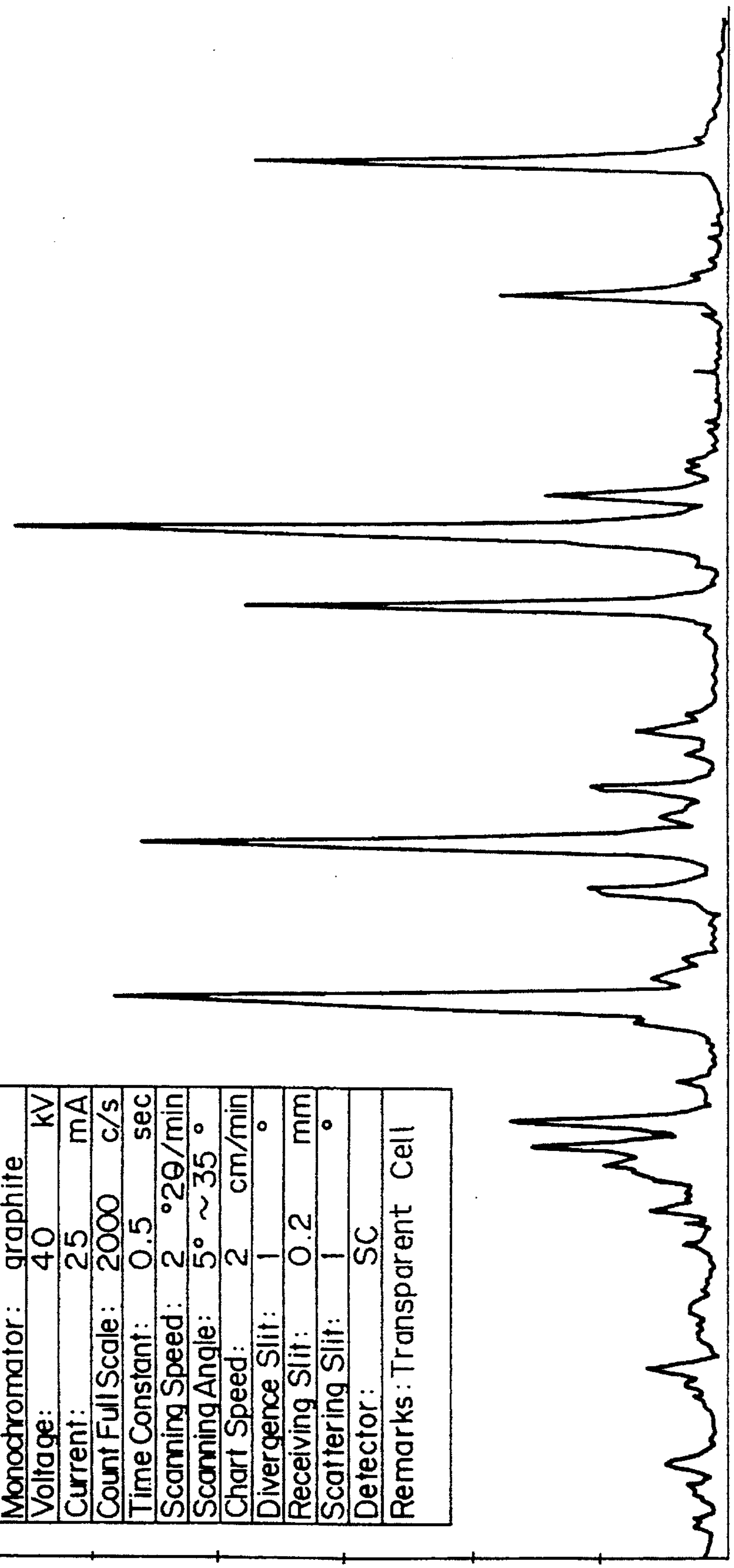
FIG. 32 shows powder X-ray diffraction spectra for type I crystal of Q-35 after blending, FIG. 32*a* showing a powder X-ray diffraction spectrum for a powder blended in ethanol, FIG. 32*b* for a powder blended in an aqueous solution of 50% ethanol, and FIG. 32*c* for a powder blended in water.
Figure 32B:
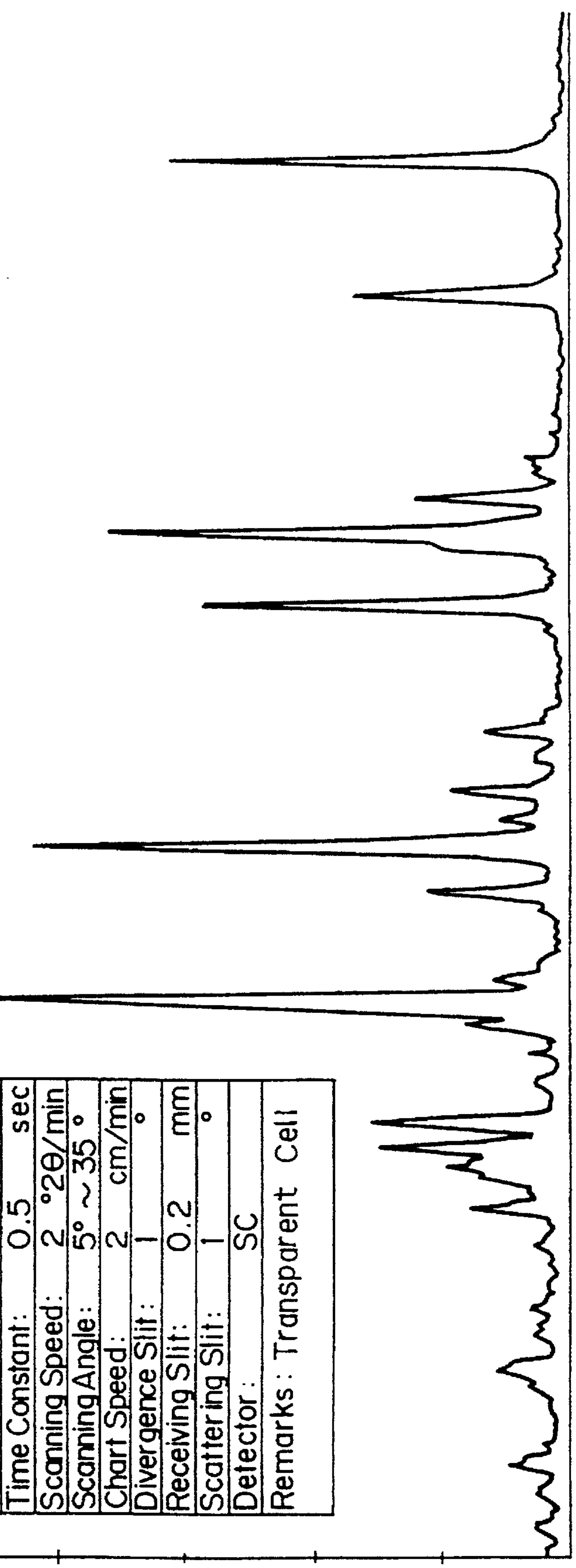
Figure 32C:
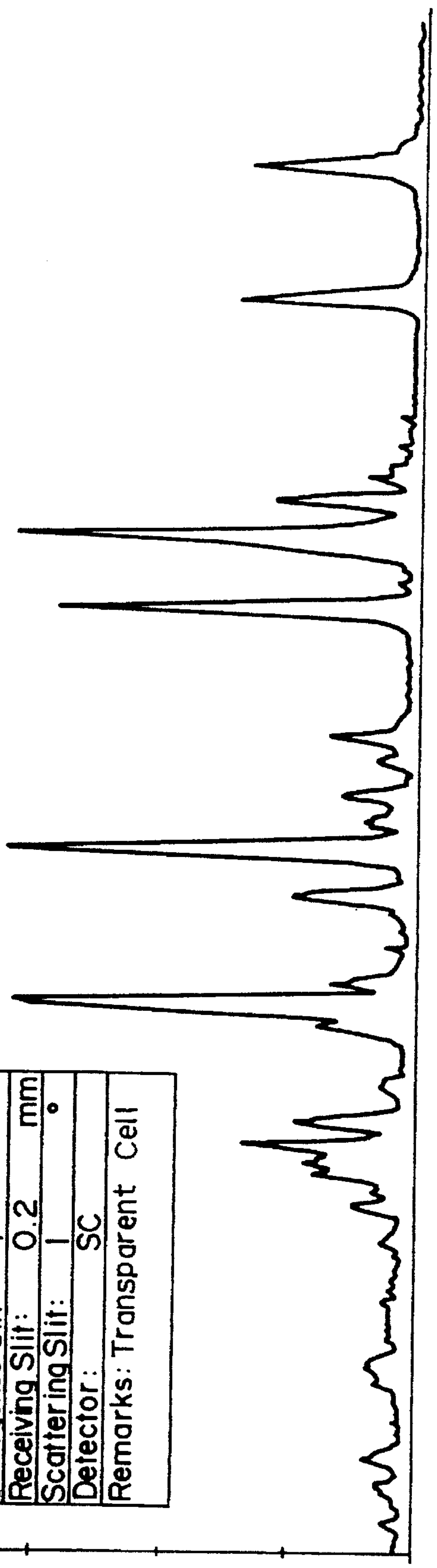

On the other hand, the powder of type I crystal produced powder X-ray diffraction spectra that agreed with the one for the initial stage of type I crystal irrespective of the solvent in which it was blended (FIG. 32). It was thus verified that the blending of type I crystal did not cause any shifting therefrom.

Therefore, type I crystal was found to be more desirable than type II crystal in pharmaceutical formulation procedures by wet granulation.

Industrial Applicability

As described on the foregoing pages, type I crystal of Q-35 according to the invention exhibits excellent stability under various conditions such as moisture absorption and blending in solvents and, hence, it is a most advantageous crystal form in pharmaceutical formulation procedures.

We claim:

1. 1-Cyclopropyl-6-fluoro-1,4-dihydro-8-methoxy-7-(3-methylaminopiperidin-1-yl)-4-oxoquinoline-3-carboxylic acid dihydrate having the following formula:

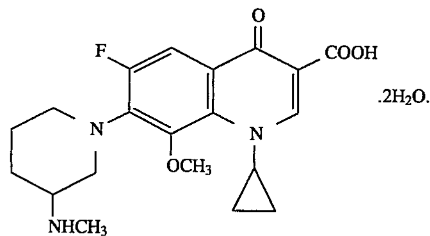

2. A pharmaceutical composition comprising an effective amount of the compound according to claim 1 and a pharmaceutically acceptable carrier.

3. 1-Cyclopropyl-6-fluoro-1,4-dihydro-8-methoxy-7-(3-methylaminopiperidin-1-yl)-4-oxoquinoline-3-carboxylic acid dihydrate which has been obtained by recrystallizing 1-cyclopropyl-6-fluoro-1,4-dihydro-8-methoxy-7-(3-methylaminopiperidin-1-yl)-4-oxoquinoline-3-carboxylic acid from a 50:50 mixture of water and ethanol.

* * * * *

UNITED STATES PATENT AND TRADEMARK OFFICE
CERTIFICATE OF CORRECTION

PATENT NO. : 5,597,923
DATED : January 28, 1997
INVENTOR(S) : Hiroyuki NAGANO et al.

It is certified that error appears in the above-indentified patent and that said Letters Patent is hereby corrected as shown below:

Cover page, item [22], delete "31" and insert therefor --29--.

Signed and Sealed this

Thirteenth Day of May, 1997

Attest:

BRUCE LEHMAN

Attesting Officer

*Commissioner of Patents and Trademarks*